United States Patent
Hindupur et al.

(10) Patent No.: US 9,193,698 B2
(45) Date of Patent: Nov. 24, 2015

(54) PROCESS FOR PREPARING FLUOXASTROBIN

(71) Applicant: Arysta LifeScience Corporation, Tokyo (JP)

(72) Inventors: Rama Mohan Hindupur, Hyderabad (IN); Avinash Sheshrao Mane, Bangalore (IN); Sankar Balakrishnan, Tamilnadu (IN); Jivan Dhanraj Pawar, Karnataka (IN); Mahagundappa Rachappa Maddani, Karnataka (IN); Sandeep Wadhwa, Berkshire (GB); Vic Prasad, Leawood, KS (US)

(73) Assignee: ADVINUS THERAPEUTICS, LTD. (IN)

( * ) Notice: Subject to any disclaimer, the term of this patent is extended or adjusted under 35 U.S.C. 154(b) by 0 days.

(21) Appl. No.: 14/323,413

(22) Filed: Jul. 3, 2014

(65) Prior Publication Data
US 2015/0011753 A1    Jan. 8, 2015

Related U.S. Application Data

(60) Provisional application No. 61/843,656, filed on Jul. 8, 2013.

(51) Int. Cl.
C07D 273/00    (2006.01)
A01N 43/88    (2006.01)

(52) U.S. Cl.
CPC .................................. C07D 273/00 (2013.01)

(58) Field of Classification Search
CPC .............................. C07D 273/00; A01N 43/88
USPC ........................................................... 544/65
See application file for complete search history.

(56) References Cited

U.S. PATENT DOCUMENTS

| | | | |
|---|---|---|---|
| 5,391,811 A | 2/1995 | Bohm et al. | |
| 5,516,815 A | 5/1996 | Buehler et al. | |
| 5,679,676 A | 10/1997 | Kruger et al. | |
| 5,883,250 A | 3/1999 | Kruger et al. | |
| 6,005,104 A | 12/1999 | Gallenkamp et al. | |
| 6,093,837 A | 7/2000 | Gallenkamp et al. | |

(Continued)

FOREIGN PATENT DOCUMENTS

| | | |
|---|---|---|
| CN | 100358877 C | 1/2008 |
| CN | 1803798 B | 6/2010 |

(Continued)

OTHER PUBLICATIONS

International Search Report of the International Searching Authority for International Patent Application No. PCT/US2014/045556; International Filing Date: Jul. 7, 2014; Date of Mailing: Oct. 31, 2014; 6 Pages.

(Continued)

*Primary Examiner* — Kahsay Habte
(74) *Attorney, Agent, or Firm* — Cantor Colburn LLP

(57) ABSTRACT

The disclosure includes a process for preparing fluoxastrobin which includes reacting compound (10) with an alkyl nitrite in the presence of an acid to form compound (11A); reacting compound (11A) with 2-haloethanol to form compound (12A); reacting compound (12A) with a base to form compound (13); and reacting compound (13) with compound (5) and 2-chlorophenol to produce fluoxastrobin.

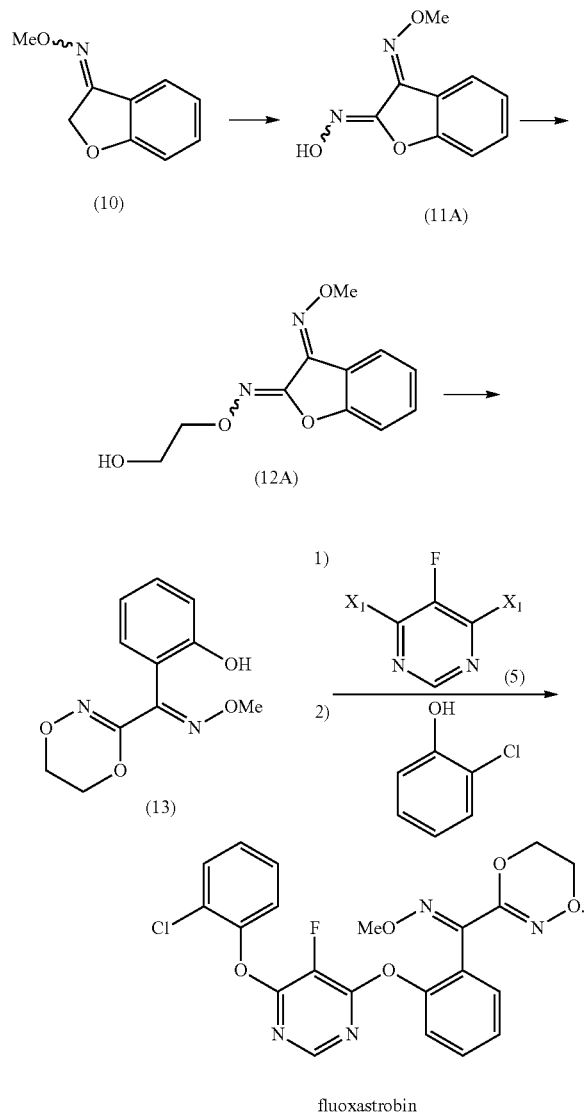

15 Claims, No Drawings

(56) References Cited

U.S. PATENT DOCUMENTS

| | | |
|---|---|---|
| 6,103,717 A | 8/2000 | Heinemann et al. |
| 6,150,521 A | 11/2000 | Gayer et al. |
| 6,191,128 B1 | 2/2001 | Stenzel et al. |
| 6,194,418 B1 | 2/2001 | Seitz et al. |
| 6,255,486 B1 | 7/2001 | Weintritt et al. |
| 6,303,598 B1 | 10/2001 | Stenzel et al. |
| 6,335,454 B1 | 1/2002 | Gallenkamp et al. |
| 6,372,737 B1 | 4/2002 | Stenzel et al. |
| 6,380,386 B2 | 4/2002 | Seitz et al. |
| 6,407,233 B1 | 6/2002 | Heinemann et al. |
| 6,437,153 B1 | 8/2002 | Gallenkamp et al. |
| 6,479,675 B1 | 11/2002 | Gayer et al. |
| 6,509,343 B1 | 1/2003 | Stenzel et al. |
| 6,603,025 B1 | 8/2003 | Lantzsch et al. |
| 6,730,799 B2 | 5/2004 | Gayer et al. |
| 6,734,304 B2 | 5/2004 | Weintritt et al. |
| 7,129,353 B2 | 10/2006 | Geller et al. |
| 7,807,851 B2 | 10/2010 | Günther et al. |
| 2008/0269051 A1 | 10/2008 | Suty-Heinze et al. |

FOREIGN PATENT DOCUMENTS

| | | |
|---|---|---|
| CN | 101239955 B | 11/2011 |
| WO | 2006021368 A1 | 3/2006 |

OTHER PUBLICATIONS

Written Opinion of the International Searching Authority for International Patent Application No. PCT/US2014/045556; International Filing Date: Jul. 7, 2014; Date of Mailing: Oct. 31, 2014; 7 Pages.

PROCESS FOR PREPARING FLUOXASTROBIN

CROSS-REFERENCE TO RELATED APPLICATION

This application claims the benefit of U.S. Provisional Application No. 61/843,656 filed Jul. 8, 2013, which is hereby incorporated by reference in its entirety.

TECHNICAL FIELD

The disclosure provides a novel process for preparing fluoxastrobin

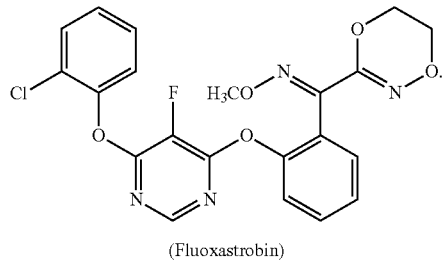 [SMILES: CO/N=C(/C1=NOCCO1)c1ccccc1Oc1ncnc(Oc2ccccc2Cl)c1F]

(Fluoxastrobin)

BACKGROUND

Fluoxastrobin is a strobilurin-type fungicidal active ingredient for the control of fungal diseases such as early blight, late blight, leaf spots, leaf rust, and *Rhizoctonia solani*. Fluoxastrobin has been registered for foliar use on peanuts, tuberous and corm vegetables, leaf petiole vegetables, fruiting vegetables, and turf, as well as seed treatment for potato, peanut and turf. Turf applications are labeled for professional pest control operators.

Bayer provides a number of synthetic pathways to fluoxastrobin, although all proceed through a consecutive reaction of 4,6-dichloro-5-fluoro-pyrimidine (5) with 2-chlorophenol and (E)-(5,6-dihydro-1,4,2-dioxazin-3-yl)(2-hydroxyphenyl)methanone O-methyl oxime (13) as described in U.S. Pat. No. 6,734,304 and shown below:

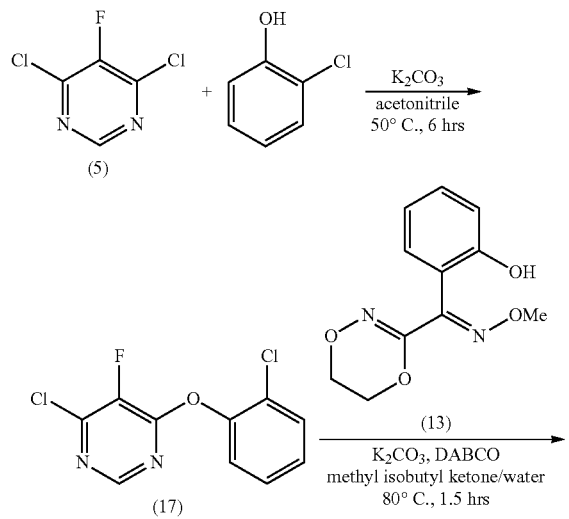

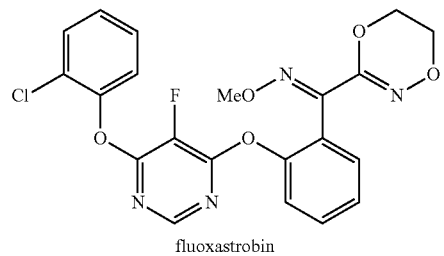

fluoxastrobin

There remains a need for novel and efficient, scalable and cost effective synthetic approaches to fluoxastrobin.

SUMMARY

The present disclosure provides a process of preparing fluoxastrobin by (i) reacting benzofuran-3(2H)-one O-methyl oxime (10) with an alkyl nitrite in the presence of an acid to form (3E)-2,3-benzofuran-dione $O^3$-methyl dioxime (11A) as a predominant isomer regioselectively;

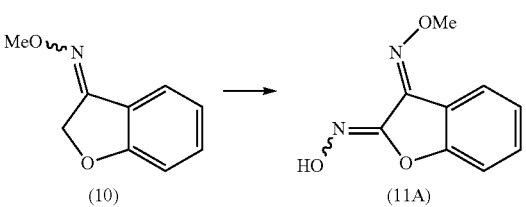 [SMILES: CON=C1COc2ccccc21 ; CO/N=C1/C(=NO)Oc2ccccc21]

(ii) reacting the (3E)-2,3-benzofuran-dione $O^3$-methyl dioxime (11A) with 2-haloethanol to form (3E)-benzofuran-2,3-dione $O^2$-(2-hydroxyethyl) $O^3$-methyl dioxime (12A); and

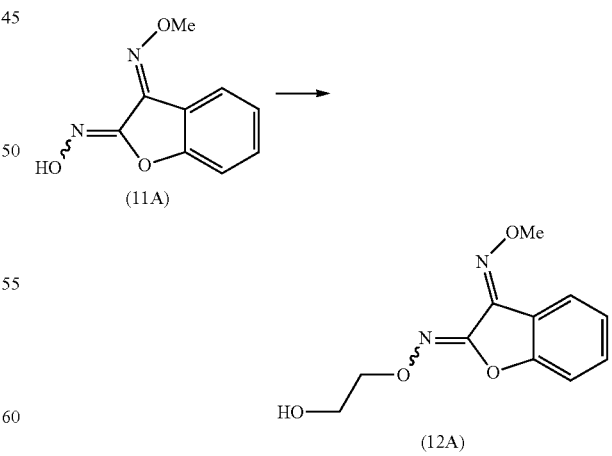

(iii) reacting the (3E)-benzofuran-2,3-dione $O^2$-(2-hydroxyethyl) $O^3$-methyl dioxime (12A) with a base to form (E)-(5,6-dihydro-1,4,2-dioxazin-3-yl)(2-hydroxyphenyl)methanone O-methyl oxime (13) regioselectively

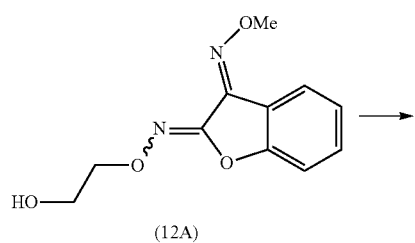

(12A)

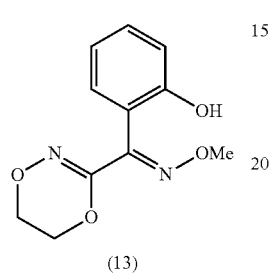

(13)

(iv) reacting a 4,6-di-halo-5-fluoro-pyrimidine (5), wherein $X_1$ is halogen, with the (E)-(5,6-dihydro-1,4,2-dioxazin-3-yl)(2-hydroxyphenyl)methanone O-methyl oxime (13), in the presence of a solvent and optionally in the presence of a base, to form an (E)-(2-((6-halo-5-fluoropyrimidin-4-yl)oxy)phenyl)(5,6-dihydro-1,4,2-dioxazin-3-yl)methanone O-methyl oxime (14):

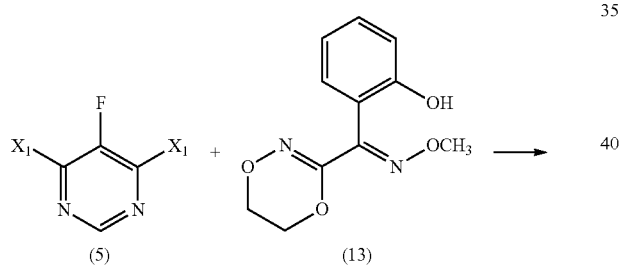

(v) reacting the (E)-(2-((6-halo-5-fluoropyrimidin-4-yl)oxy)phenyl)(5,6-dihydro-1,4,2-dioxazin-3-yl)methanone O-methyl oxime (14) with 2-chlorophenol, in the presence of a solvent and optionally in the presence of a base, to form fluoxastrobin without forming (Z)-fluoxastrobin, even in trace amounts:

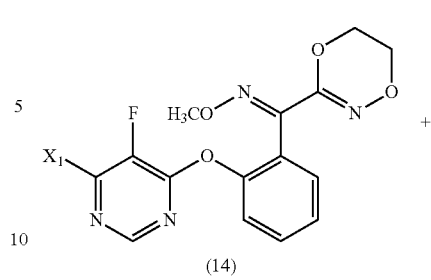

(14)

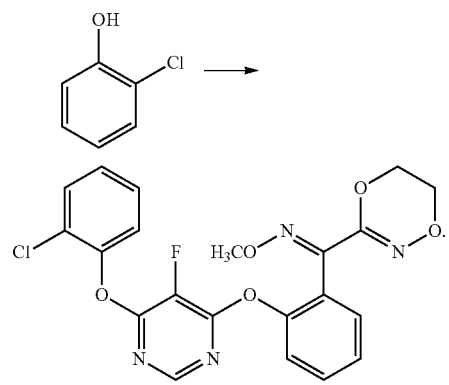

fluoxastrobin

The disclosure further provides a process for preparing fluoxastrobin, comprising:

(i) reacting a 4,6-di-halo-5-fluoro-pyrimidine (5), wherein $X_1$ is halogen, with (Z)-(5,6-dihydro-1,4,2-dioxazin-3-yl)(2-hydroxyphenyl)methanone O-methyl oxime (15), optionally in the presence of a solvent and optionally in the presence of a base, to form a (Z)-(2-((6-halo-5-fluoropyrimidin-4-yl)oxy)phenyl)(5,6-dihydro-1,4,2-dioxazin-3-yl)methanone O-methyl oxime (16):

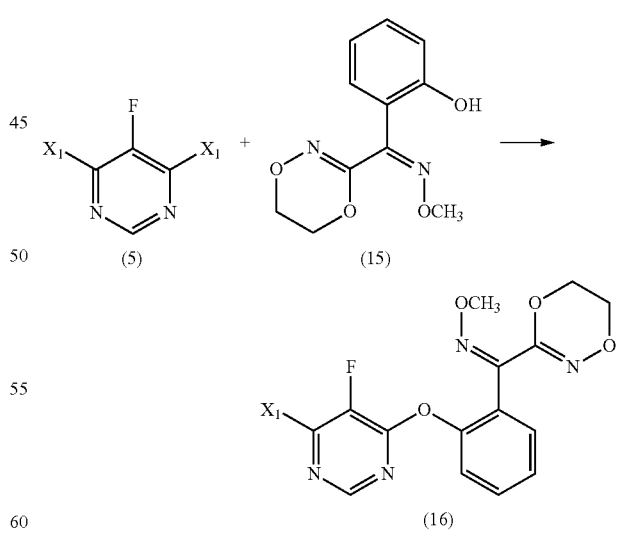

(ii) reacting the (Z)-(2-((6-halo-5-fluoropyrimidin-4-yl)oxy)phenyl)(5,6-dihydro-1,4,2-dioxazin-3-yl)methanone O-methyl oxime (16) with 2-chlorophenol, optionally in the presence of a solvent and optionally in the presence of a base, to form (Z)-fluoxastrobin:

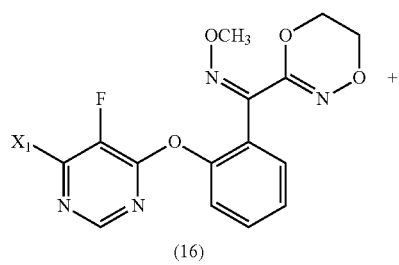

(16)

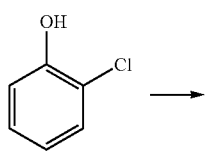

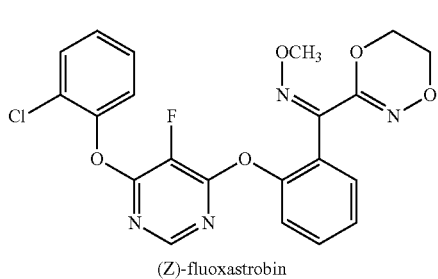

(Z)-fluoxastrobin (iii) isomerizing the (Z)-fluoxastrobin to form fluoxastrobin:

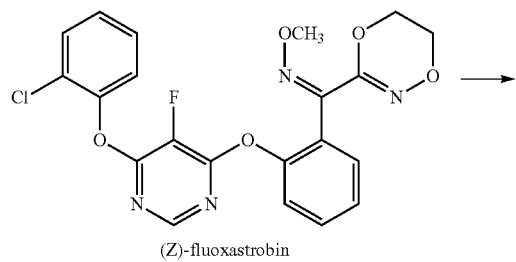

(Z)-fluoxastrobin

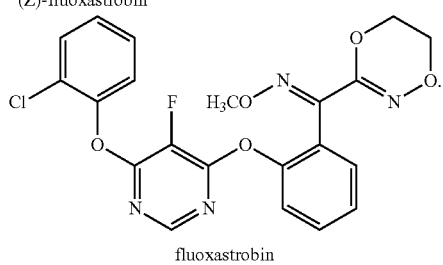

fluoxastrobin

The disclosure further provides a process for preparing fluoxastrobin, comprising:

(i) reacting a 4,6-di-halo-5-fluoro-pyrimidine (5), wherein $X_1$ is halogen, with 2-chlorophenol, optionally in the presence of a solvent and optionally in the presence of a base, to form a 4-halo-6-(2-chlorophenoxy)-5-fluoropyrimidine (17):

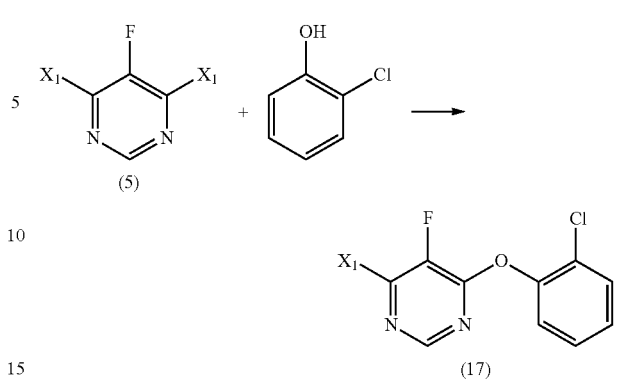

(ii) reacting the 4-halo-6-(2-chlorophenoxy)-5-fluoropyrimidine (17) with (Z)-(5,6-dihydro-1,4,2-dioxazin-3-yl)(2-hydroxyphenyl)methanone O-methyl oxime (15), optionally in the presence of a solvent and optionally in the presence of a base, to form (Z)-fluoxastrobin:

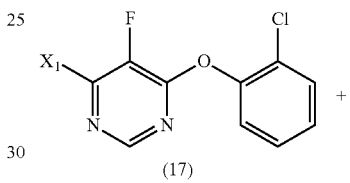

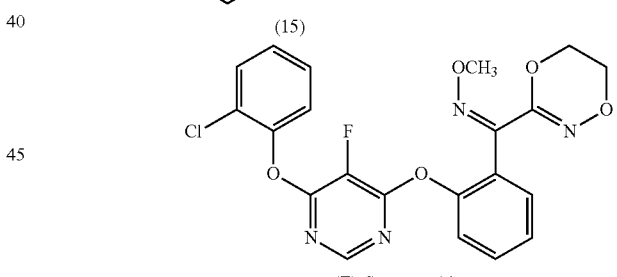

(Z)-fluoxastrobin (iii) isomerizing the (Z)-fluoxastrobin to form fluoxastrobin:

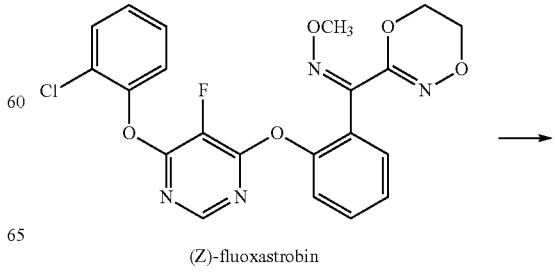

(Z)-fluoxastrobin

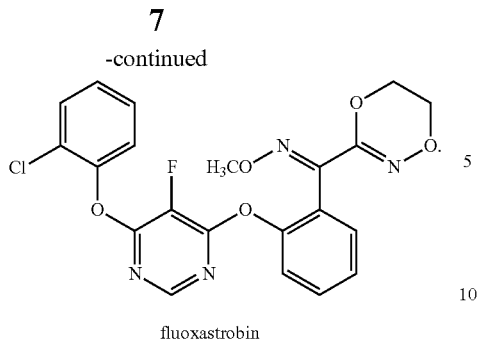

fluoxastrobin

The disclosure further provides a process for preparing (E)-(5,6-dihydro-1,4,2-dioxazin-3-yl)(2-hydroxyphenyl) methanone O-methyl oxime (13)

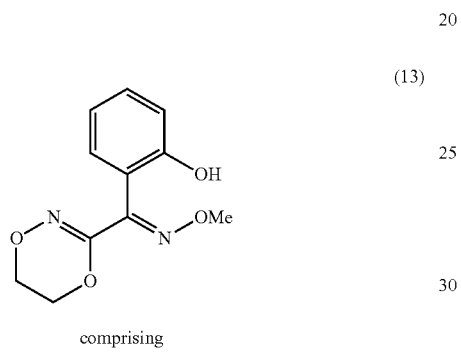

(13)

comprising (i) reacting benzofuran-3(2H)-one O-methyl oxime (10) with an alkyl nitrite in the presence of an acid to form (3E)-2,3-benzofuran-dione $O^3$-methyl dioxime (11A) as a predominant isomer regioselectively;

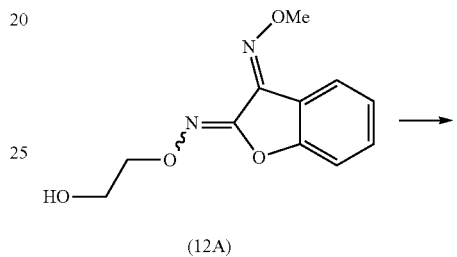

(ii) reacting the (3E)-2,3-benzofuran-dione $O^3$-methyl dioxime (11A) with 2-haloethanol to form (3E)-benzofuran-2,3-dione $O^2$-(2-hydroxyethyl) $O^3$-methyl dioxime (12A); and

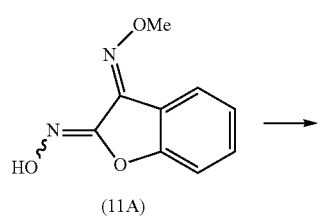

(11A)

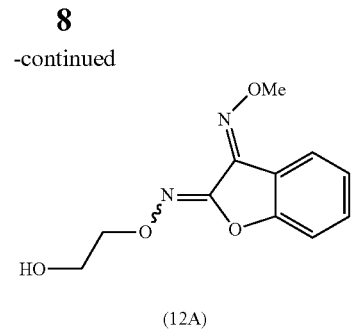

(12A)

(iii) reacting the (3E)-benzofuran-2,3-dione $O^2$-(2-hydroxyethyl) $O^3$-methyl dioxime (12A) with a base to form (E)-(5,6-dihydro-1,4,2-dioxazin-3-yl)(2-hydroxyphenyl) methanone O-methyl oxime (13) regioselectively

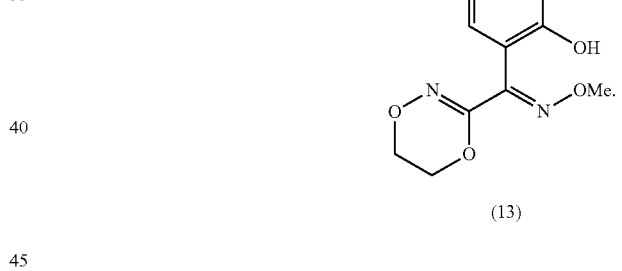

(13)

The disclosure further provides a process of preparing (Z)-(5,6-dihydro-1,4,2-dioxazin-3-yl)(2-hydroxyphenyl) methanone O-methyl oxime (15) regioselectively

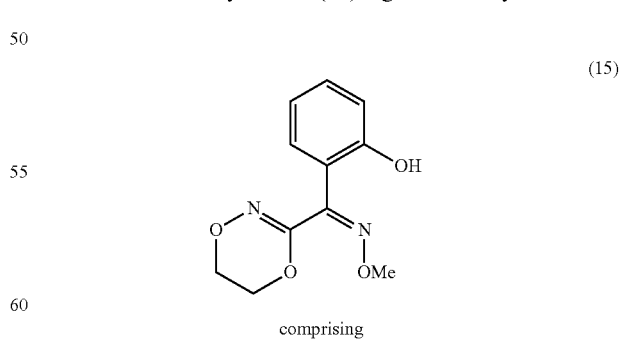

comprising (i) reacting benzofuran-3(2H)-one O-methyl oxime (10) with an alkyl nitrite in the presence of a base to form (3Z)-2,3-benzofuran-dione $O^3$-methyl dioxime (11B) as a predominant isomer regioselectively;

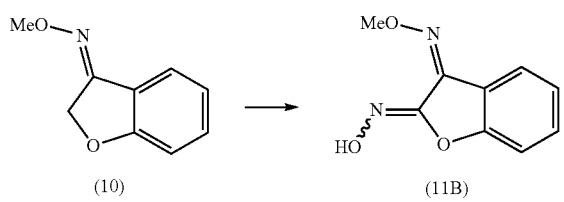 [SMILES: CO/N=C1\COc2ccccc21 ; CO/N=C1\C(=NO)Oc2ccccc21]

(ii) reacting the (3Z)-2,3-benzofuran-dione $O^3$-methyl dioxime (11B) with 2-haloethanol to form (3Z)-benzofuran-2,3-dione $O^2$-(2-hydroxyethyl) $O^3$-methyl dioxime (12B); and

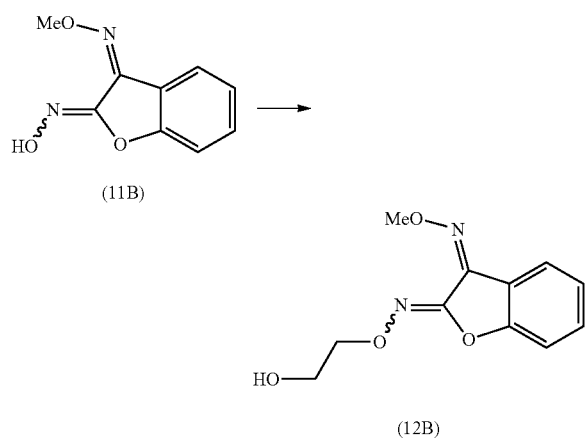 [SMILES: CO/N=C1\C(=NO)Oc2ccccc21 ; CO/N=C1\C(=NOCCO)Oc2ccccc21]

reacting the (3Z)-benzofuran-2,3-dione $O^2$-(2-hydroxyethyl) $O^3$-methyl dioxime (12B) to form (Z)-(5,6-dihydro-1,4,2-dioxazin-3-yl)(2-hydroxyphenyl)methanone O-methyl oxime (15) regioselectively

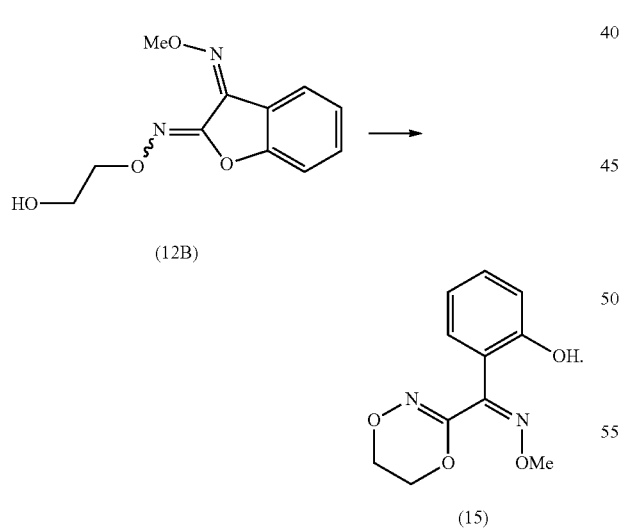

DETAILED DESCRIPTION

The invention now will be described more fully hereinafter with reference to the accompanying drawings. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

A process for preparing fluoxastrobin includes:

(i) reacting benzofuran-3(2H)-one O-methyl oxime (10) with an alkyl nitrite in the presence of an acid to form (3E)-2,3-benzofuran-dione $O^3$-methyl dioxime (11A) as a predominant isomer regioselectively;

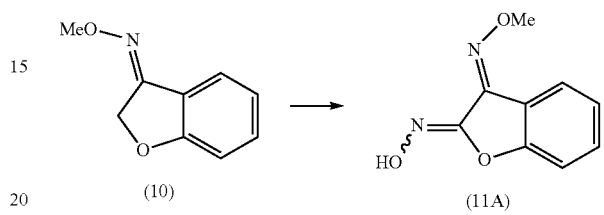

(ii) reacting the (3E)-2,3-benzofuran-dione $O^3$-methyl dioxime (11A) with 2-haloethanol to form (3E)-benzofuran-2,3-dione $O^2$-(2-hydroxyethyl) $O^3$-methyl dioxime (12A); and

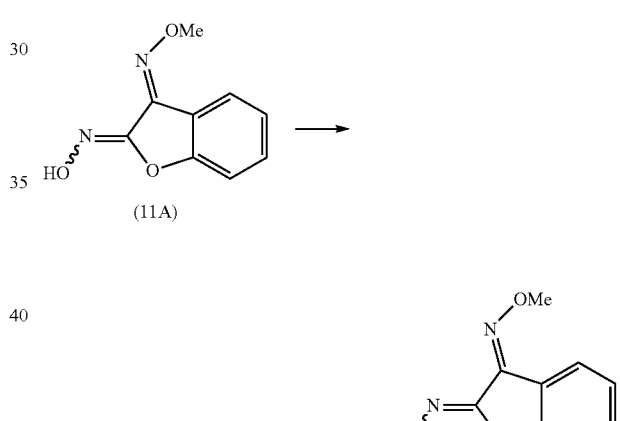

(iii) reacting the (3E)-benzofuran-2,3-dione $O^2$-(2-hydroxyethyl) $O^3$-methyl dioxime (12A) with a base to form (E)-(5,6-dihydro-1,4,2-dioxazin-3-yl)(2-hydroxyphenyl)methanone O-methyl oxime (13) regioselectively

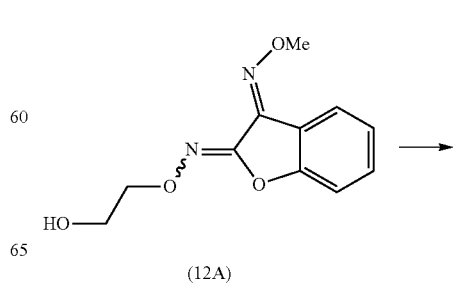

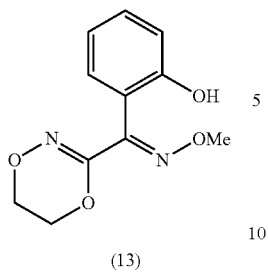

(13)

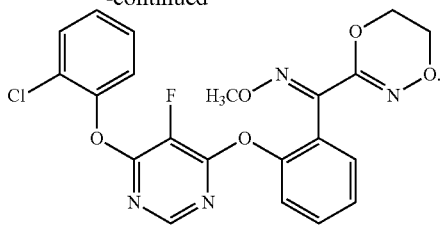

fluoxastrobin (iv) reacting a 4,6-di-halo-5-fluoro-pyrimidine (5), wherein $X_1$ is halogen, with the (E)-(5,6-dihydro-1,4,2-dioxazin-3-yl)(2-hydroxyphenyl)methanone O-methyl oxime (13), in the presence of a solvent and optionally in the presence of a base, to form an (E)-(2-((6-halo-5-fluoropyrimidin-4-yl)oxy)phenyl)(5,6-dihydro-1,4,2-dioxazin-3-yl)methanone O-methyl oxime (14):

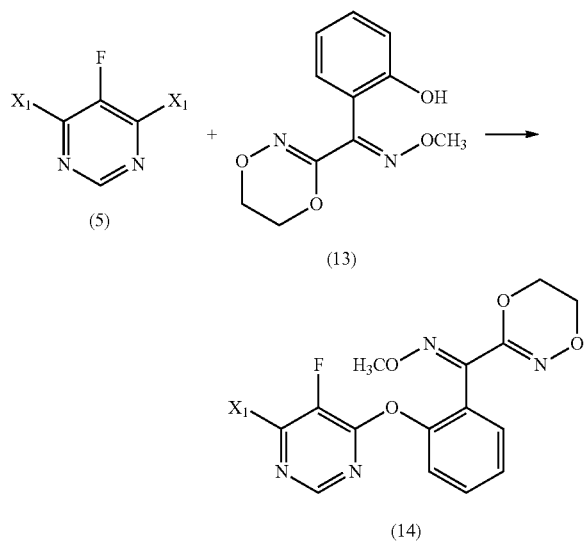

(v) reacting the (E)-(2-((6-halo-5-fluoropyrimidin-4-yl)oxy)phenyl)(5,6-dihydro-1,4,2-dioxazin-3-yl)methanone O-methyl oxime (14) with 2-chlorophenol, in the presence of a solvent and optionally in the presence of a base, to form fluoxastrobin:

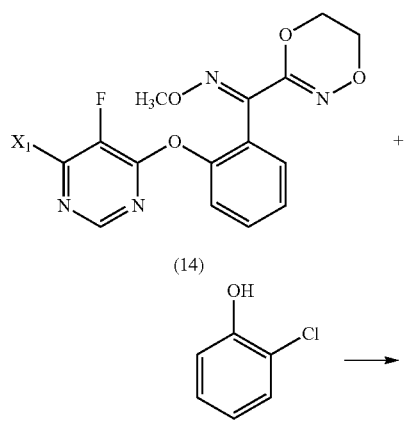

In the above process, benzofuran-3(2H)-one O-methyl oxime (10) may be reacted with an alkyl nitrite in the presence of a solvent, and optionally in the presence of an acid, to form (3E)-2,3-benzofuran-dione $O^3$-methyl dioxime (11A) exclusively or as a predominant isomer in a mixture of (3E)-2,3-benzofuran-dione $O^3$-methyl dioxime (11A) and (3E)-2,3-benzofuran-dione $O^3$-methyl dioxime (11B). The alkyl nitrite may be n-butyl nitrite or t-butyl nitrite. The acid may be hydrochloric acid, sulfuric acid, methanesulfonic acid, phosphoric acid, or a combination thereof. The solvent may be an ester solvent, for example, methyl acetate, ethyl acetate, isopropyl acetate, n-butyl acetate, or a combination thereof.

In an embodiment, a content of the (3E)-2,3-benzofuran-dione $O^3$-methyl dioxime (11A) in the mixture of (3E)- and (3Z)-isomers (11A) and (11B) respectively may be from 90% to 94%. The content of the (3E)-2,3-benzofuran-dione $O^3$-methyl dioxime (11A) in the mixture of isomers may be determined by a variety of analytical methods known to one of ordinary skill in the art. For example, the content of the (3E)-2,3-benzofuran-dione $O^3$-methyl dioxime (11A) in the mixture of (3E)- and (3Z)-isomers may be determined by an HPLC method.

The reacting of benzofuran-3(2H)-one O-methyl oxime (10) with an alkyl nitrite to form (3E)-2,3-benzofuran-dione $O^3$-methyl dioxime (11A) may be carried out at a temperature of about 0° C. to about 60° C., and specifically about 0° C. to about 40° C.

According to the above process, the (3E)-2,3-benzofuran-dione $O^3$-methyl dioxime (11A) may be reacted with 2-haloethanol in the presence of a solvent, and optionally in the presence of a base, to form (3E)-benzofuran-2,3-dione $O^2$-(2-hydroxyethyl) $O^3$-methyl dioxime (12A). The 2-haloethanol may be 2-chloroethanol or 2-bromoethanol. The base may be a metal hydroxide, such as lithium hydroxide, sodium hydroxide, potassium hydroxide, or a combination thereof. The solvent may be a ketone solvent, a nitrile solvent, an amide solvent, a sulfoxide solvent, a sulfone solvent, water, or a combination of these solvents. Non-limiting examples of the ketone solvent include acetone, methyl ethyl ketone, and methyl isobutyl ketone. Non-limiting example of the nitrile solvent include acetonitrile. Non-limiting examples of the amide solvent include N,N-dimethylformamide ("DMF"), N,N-dimethylacetamide ("DME"), N-methylformamide, N-methylpyrrolidone ("NMP"), and hexamethylphosphoric triamide ("HMPA"). Non-limiting example of the sulfoxide solvent include dimethyl sulfoxide ("DMSO"). Non-limiting example of the sulfone solvent include sulfolane.

The reacting of (3E)-2,3-benzofuran-dione $O^3$-methyl dioxime (11A) with 2-haloethanol to form (3E)-benzofuran-2,3-dione $O^2$-(2-hydroxyethyl) $O^3$-methyl dioxime (12A) may be carried out at a temperature of about 20° C. to about 100° C., and specifically about 70° C. to about 85° C.

According to the above process, (3E)-benzofuran-2,3-dione $O^2$-(2-hydroxyethyl) $O^3$-methyl dioxime (12A) may be treated with a base to form (E)-(5,6-dihydro-1,4,2-dioxazin-3-yl)(2-hydroxyphenyl)methanone O-methyl oxime (13). The base may be a metal hydroxide, such as lithium hydroxide, sodium hydroxide, potassium hydroxide, or a combination thereof.

The reacting of (3E)-benzofuran-2,3-dione $O^2$-(2-hydroxyethyl) $O^3$-methyl dioxime (12A) to form (E)-(5,6-dihydro-1,4,2-dioxazin-3-yl)(2-hydroxyphenyl)methanone O-methyl oxime (13) may be carried out at a temperature of about 20° C. to about 100° C., and specifically about 65° C. to about 75° C.

In the above process, $X_1$ may be fluorine, chlorine, bromine, and iodine. Specifically, $X_1$ may be chlorine.

The step of reacting the (E)-(2-((6-halo-5-fluoropyrimidin-4-yl)oxy)phenyl)(5,6-dihydro-1,4,2-dioxazin-3-yl)methanone O-methyl oxime (14) with 2-chlorophenol may be carried out in the presence of a tertiary amine, specifically 1,4-diazabicyclo[2.2.2]octane ("DABCO"), 1,5-diazobicyclo[4.3.0]non-5-ene ("DBN"), or 1,8-diazobicyclo[5.4.0]undec-7-ene ("DBU"), and more specifically, 1,4-diazabicyclo[2.2.2]octane ("DABCO").

In an embodiment, an amount of 1,4-diazabicyclo[2.2.2]octane may be from about 0.02 to about 0.4 moles per mole of the (E)-(2-((6-halo-5-fluoropyrimidin-4-yl)oxy)phenyl)(5,6-dihydro-1,4,2-dioxazin-3-yl)methanone O-methyl oxime (14).

In another embodiment, the amount of 1,4-diazabicyclo[2.2.2]octane is from about 0.02 to about 0.2 moles per mole of the (E)-(2-((6-halo-5-fluoropyrimidin-4-yl)oxy)phenyl)(5,6-dihydro-1,4,2-dioxazin-3-yl)methanone O-methyl oxime (14).

Steps (ii), (iii), (iv), and (v) in the process for preparing fluoxastrobin may be carried out as a one-pot process, i.e. without isolation and purification of intermediate products (12A), (13), and (14).

In the step of reacting a 4,6-di-halo-5-fluoro-pyrimidine (5), wherein $X_1$ is halogen, with (E)-(5,6-dihydro-1,4,2-dioxazin-3-yl)(2-hydroxyphenyl)methanone O-methyl oxime (13), an amount of the 4,6-di-halo-5-fluoro-pyrimidine (5) may be from about 1 to about 4 moles per one mole of the (E)-(5,6-dihydro-1,4,2-dioxazin-3-yl)(2-hydroxyphenyl)methanone O-methyl oxime (13).

In the step of reacting of the (E)-(2-((6-halo-5-fluoropyrimidin-4-yl)oxy)phenyl)(5,6-dihydro-1,4,2-dioxazin-3-yl)methanone O-methyl oxime (14) with 2-chlorophenol, an amount of 2-chlorophenol may be from about 0.8 to about 4 moles per one mole of the (E)-(2-((6-halo-5-fluoropyrimidin-4-yl)oxy)phenyl)(5,6-dihydro-1,4,2-dioxazin-3-yl)methanone O-methyl oxime (14).

Steps (iv) and (v) of the process for preparing fluoxastrobin may be carried out in the presence of a solvent. In an embodiment, the solvent may include a hydrocarbon solvent, a halogenated hydrocarbon solvent, an ether solvent, a ketone solvent, a nitrile solvent, an amide solvent, an ester solvent, a sulfoxide solvent, a sulfone solvent, water, or a combination thereof. The hydrocarbon solvent may include an aliphatic solvent, an alicyclic solvent, an aromatic solvent, or a combination thereof. Non-limiting examples of the hydrocarbon solvent include petroleum ether, pentane, hexane, heptane, cyclohexane, methylcyclohexane, benzene, toluene, 1,2-xylene, 1,3-xylene, 1,4-xylene, ethylbenzene, and cumene. Non-limiting examples of the halogenated solvent include chlorobenzene, dichlorobenzene, dichloromethane, chloroform, carbon tetrachloride, 1,1-dichloro ethane, 1,2-dichloroethane, 1,1,1-trichloroethane, and 1,1,2-trichloroethane. Non-limiting examples of the ether solvent include diethyl ether, diisopropyl ether, methyl-tert-butyl ether, methyl-tert-amyl ether, 1,4-dioxane, tetrahydrofuran ("THF"), 2-methyltetrahydrofuran, 1,2-dimethoxyethane ("DME"), and anisole. Non-limiting examples of the ketone solvent include acetone, 2-butanone, methyl isobutyl ketone, cyclopentanone, and cyclohexanone. In an embodiment, the ketone solvent may include methyl isobutyl ketone. Non-limiting examples of the nitrile solvent include acetonitrile ("ACN"), propionitrile, n-butyronitrile, iso-butyronitrile, and benzonitrile. Non-limiting examples of the amide solvent include N,N-dimethylformamide ("DMF"), N,N-dimethylacetamide ("DMA"), N-methylformamide, N-methylpyrrolidone ("NMP"), and hexamethylphosphoric triamide ("HMPA"). Non-limiting examples of the ester solvent include methyl acetate and ethyl acetate. Non-limiting example of the sulfoxide solvent include dimethyl sulfoxide ("DMSO"). Non-limiting example of the sulfone solvent include sulfolane.

In an embodiment, the solvent may be a mixture of the hydrocarbon solvent and the amide solvent.

For example, the solvent may be a mixture of the aromatic hydrocarbon solvent and the amide solvent. Non-limiting examples of the aromatic hydrocarbon solvent in this mixture may include benzene, toluene, 1,2-xylene, 1,3-xylene, 1,4-xylene, ethylbenzene, and cumene. Non-limiting examples of the amide solvent may include N,N-dimethylformamide ("DMF"), N,N-dimethylacetamide ("DME"), N-methylformamide, N-methylpyrrolidone ("NMP"), and hexamethylphosphoric triamide ("HMPA"). Specifically, the solvent may be a mixture of the aromatic hydrocarbon solvent such as any xylene or toluene and the amide solvent, which may be for example, N,N-dimethylformamide ("DMF"), N,N-dimethylacetamide ("DME"), N-methylformamide, N-methylpyrrolidone ("NMP"), or hexamethylphosphoric triamide ("HMPA"). More specifically, the solvent may be a mixture of the aromatic hydrocarbon solvent such as any xylene and the amide solvent, for example N,N-dimethylformamide ("DMF"), N,N-dimethylacetamide ("DME"), N-methylformamide, N-methylpyrrolidone ("NMP"), or hexamethylphosphoric triamide ("HMPA"). Also more specifically, the solvent may be a mixture of the aromatic hydrocarbon solvent such as toluene and the amide solvent such as N,N-dimethylformamide ("DMF"), N,N-dimethylacetamide ("DME"), N-methylformamide, N-methylpyrrolidone ("NMP"), or hexamethylphosphoric triamide ("HMPA").

Furthermore, steps (iv) and (v) of the process for preparing fluoxastrobin may be carried out in the presence of a base. In an embodiment, the base may include an inorganic base, an organic base, or a combination thereof. The inorganic base may include a hydroxide, a hydride, an acetate, a carbonate, a bicarbonate, or a combination thereof. Non-limiting examples of the inorganic base include sodium hydroxide, potassium hydroxide, sodium hydride, potassium hydride, calcium hydride, sodium acetate, potassium acetate, sodium carbonate, potassium carbonate, rubidium carbonate, cesium carbonate, sodium bicarbonate, and potassium bicarbonate. Non-limiting examples of the organic base include trimethylamine, triethylamine, tributylamine, N,N-dimethylamine, N,N-di-iso-propylethylamine, N,N-dimethylbenzylamine, pyridine, 2-methylpyridine (2-picoline), 2,6-dimethylpyridine (2,6-lutidine), N-methylpiperidine, N-methylmorpholine ("NMM"), N,N-dimethylaminopyridine ("DMAP"), 1,5-diazobicyclo[4.3.0]non-5-ene ("DBN"), and 1,8-diazobicyclo[5.4.0]undec-7-ene ("DBU").

In the process for preparing fluoxastrobin, the step of reacting a 4,6-di-halo-5-fluoro-pyrimidine (5), wherein $X_1$ is halogen, with (E)-(5,6-dihydro-1,4,2-dioxazin-3-yl)(2-hydroxyphenyl)methanone O-methyl oxime (13) may be carried out at a temperature of about 0° C. to about 100° C., and specifically about 40° C. to about 80° C. The reaction time may vary from about 1 to about 10 hours, specifically from about 1 to about 6 hours.

Also, in the process for preparing fluoxastrobin, the step of reacting the (E)-(2-((6-halo-5-fluoropyrimidin-4-yl)oxy) phenyl)(5,6-dihydro-1,4,2-dioxazin-3-yl)methanone O-methyl oxime (14) with 2-chlorophenol may be carried out at a temperature of about 0° C. to about 100° C., specifically about 40° C. to about 90° C., and more specifically about 50° C. to about 80° C. The reaction time may vary from about 15 min to about 3 hours, specifically from about 30 min to about 1.5 hours.

Another process for preparing fluoxastrobin, provided by this disclosure, includes:

(i) reacting a 4,6-di-halo-5-fluoro-pyrimidine (5), wherein $X_1$ is halogen, with (Z)-(5,6-dihydro-1,4,2-dioxazin-3-yl)(2-hydroxyphenyl)methanone O-methyl oxime (15), optionally in the presence of a solvent and optionally in the presence of a base, to form a (Z)-(2-((6-halo-5-fluoropyrimidin-4-yl) oxy)phenyl)(5,6-dihydro-1,4,2-dioxazin-3-yl)methanone O-methyl oxime (16):

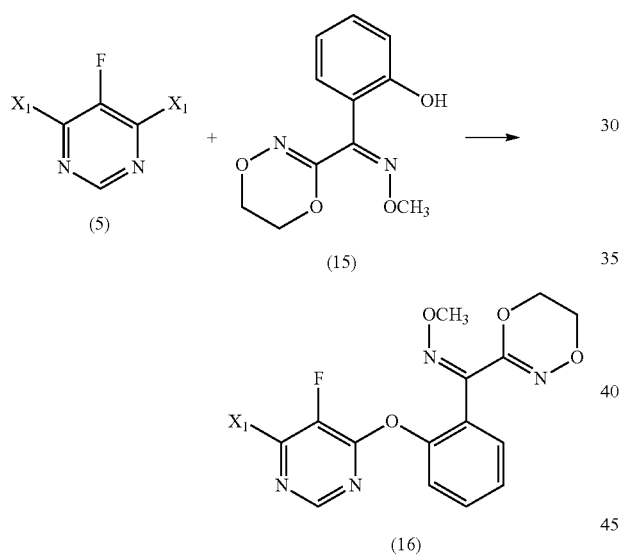

(ii) reacting the (Z)-(2-((6-halo-5-fluoropyrimidin-4-yl) oxy)phenyl)(5,6-dihydro-1,4,2-dioxazin-3-yl)methanone O-methyl oxime (16) with 2-chlorophenol, optionally in the presence of a solvent and optionally in the presence of a base, to form (Z)-fluoxastrobin:

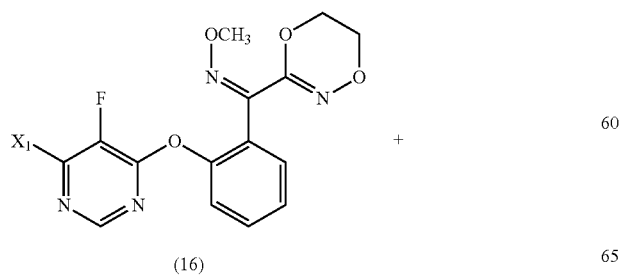

(iii) isomerizing (Z)-fluoxastrobin to form fluoxastrobin:

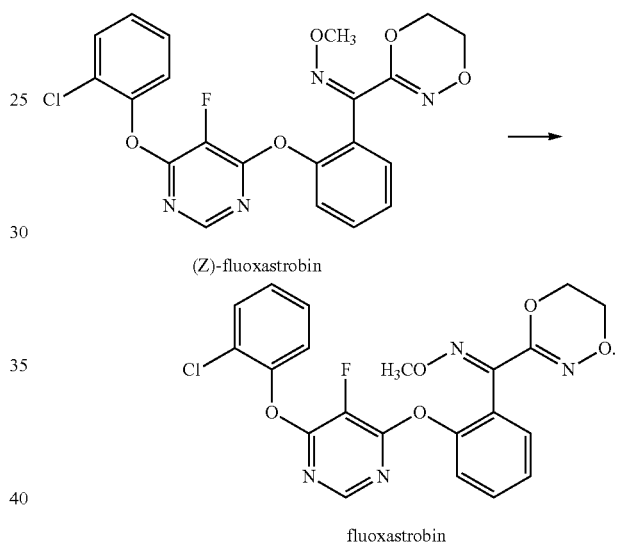

Yet another process for preparing fluoxastrobin, of this disclosure, includes:

(i) reacting a 4,6-di-halo-5-fluoro-pyrimidine (5), wherein $X_1$ is halogen, with 2-chlorophenol, optionally in the presence of a solvent and optionally in the presence of a base, to form a 4-halo-6-(2-chlorophenoxy)-5-fluoropyrimidine (17):

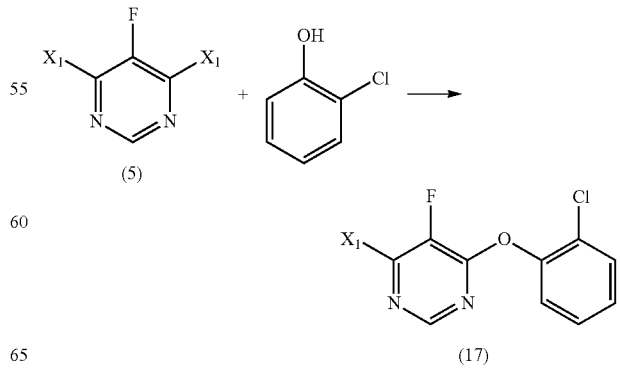

(ii) reacting the 4-halo-6-(2-chlorophenoxy)-5-fluoropyrimidine (17) with (Z)-(5,6-dihydro-1,4,2-dioxazin-3-yl)(2-hydroxyphenyl)methanone O-methyl oxime (15), optionally in the presence of a solvent and optionally in the presence of a base, to form (Z)-fluoxastrobin:

(iii) isomerizing (Z)-fluoxastrobin to form fluoxastrobin:

The step of isomerizing (Z)-fluoxastrobin to form fluoxastrobin may be carried out in the presence of a solvent, and optionally an acid catalyst.

The acid catalyst for the isomerizing (Z)-fluoxastrobin to fluoxastrobin may be an organic acid, an inorganic acid, or a mixture thereof. Non-limiting example of the organic acid may be methanesulfonic acid. Non-limiting examples of the inorganic acid include sulfuric acid and phosphoric acid. An amount of the acid catalyst may be from about 0.2 moles to about 1.5 moles per one mole of (Z)-fluoxastrobin. Specifically, the amount of the acid catalyst may be from about 0.8 moles to about 1.1 moles per one mole of (Z)-fluoxastrobin.

The solvent used for the isomerizing (Z)-fluoxastrobin to fluoxastrobin may be a nitrile solvent, an amide solvent, a sulfoxide solvent, and ester solvent, or a combination thereof. A non-limiting example of the nitrile solvent may include acetonitrile. Non-limiting examples of the amide solvent include N,N-dimethylformamide ("DMF"), N,N-dimethylacetamide ("DME"), N-methylformamide, N-methylpyrrolidone ("NMP"), and hexamethylphosphoric triamide ("HMPA"). Non-limiting example of the sulfoxide solvent include dimethyl sulfoxide ("DMSO"). Non-limiting examples of the ester solvent include methyl acetate, ethyl acetate, isopropyl acetate, and n-butyl acetate.

The (Z)-(5,6-dihydro-1,4,2-dioxazin-3-yl)(2-hydroxyphenyl)methanone O-methyl oxime (15) in the above process may be prepared by:

(i) reacting benzofuran-3(2H)-one O-methyl oxime (10) with an alkyl nitrite in the presence of a base to form (Z)-2,3-benzofuran-dione $O^3$-methyldioxime (11B) as a predominant isomer;

reacting the (Z)-2,3-benzofuran-dione $O^3$-methyl dioxime (11B) with 2-haloethanol to form (Z)-benzofuran-2,3-dione $O^2$-(2-hydroxyethyl) $O^3$-methyl dioxime (12B); and reacting the (Z)-benzofuran-2,3-dione $O^2$-(2-hydroxyethyl) $O^3$-methyl dioxime (12B) with a base to form (Z)-(5,6-dihydro-1,4,2-dioxazin-3-yl)(2-hydroxyphenyl)methanone O-methyl oxime (15)

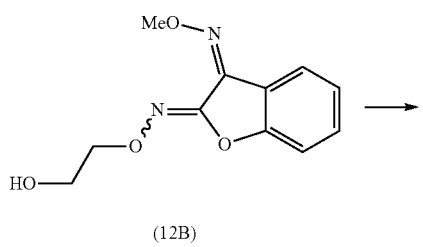

(12B)

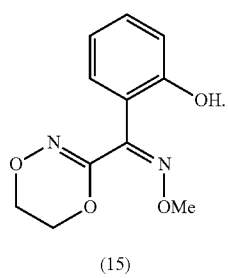

(15)

In the above process, benzofuran-3(2H)-one O-methyl oxime (10) may be reacted with an alkyl nitrite in the presence of a solvent, and optionally in the presence of a base, to form (Z)-2,3-benzofuran-dione $O^3$-methyl dioxime (11B) exclusively or as a predominant isomer in a mixture of (E)-2,3-benzofuran-dione $O^3$-methyl dioxime (11A) and (Z)-2,3-benzofuran-dione $O^3$-methyl dioxime (11B). The alkyl nitrite may be n-butyl nitrite or t-butyl nitrite. The base may be a metal hydroxide, a metal hydride, a metal alkoxide, or a combination thereof. The metal hydroxide may be lithium hydroxide, sodium hydroxide, potassium hydroxide, or a combination thereof. The metal hydride may be sodium hydride. The metal alkoxide may be potassium t-butoxide. The solvent may be an ester solvent, a sulfoxide solvent, or a combination thereof. Non-limiting examples of the amide solvent include N,N-dimethylformamide ("DMF"), N,N-dimethylacetamide ("DME"), N-methylformamide, N-methylpyrrolidone ("NMP"), and hexamethylphosphoric triamide ("HMPA"). Non-limiting example of the sulfoxide solvent include dimethyl sulfoxide ("DMSO").

A content of the (3Z)-2,3-benzofuran-dione $O^3$-methyl dioxime (11B) in the mixture of the (3E)- and (3Z)-isomers (11A) and (11B) respectively may be from 95% to 98%. The content of the (3Z)-2,3-benzofuran-dione $O^3$-methyl dioxime (11B) in the mixture of (3E)- and (3Z)-isomers may be determined by a variety of analytical methods known to one of ordinary skill in the art. For example, the content of the (3Z)-2,3-benzofuran-dione $O^3$-methyl dioxime (11B) in a mixture of the (3E)- and (3Z)-isomers may be determined by an HPLC method.

The reaction of benzofuran-3(2H)-one O-methyl oxime (10) with an alkyl nitrite to form (Z)-2,3-benzofuran-dione $O^3$-methyl dioxime (11B) may be carried out at a temperature of about 5° C. to about 60° C., and specifically about 20° C. to about 40° C.

In the above process, the (Z)-2,3-benzofuran-dione $O^3$-methyl dioxime (11B) may be reacted with 2-haloethanol in the presence of a solvent, and optionally in the presence of a base, to form (Z)-benzofuran-2,3-dione $O^2$-(2-hydroxyethyl) $O^3$-methyl dioxime (12B). The 2-haloethanol may be 2-chloroethanol or 2-bromoethanol. The base may be a metal hydroxide, such as lithium hydroxide, sodium hydroxide, potassium hydroxide, or a combination thereof. The solvent may be a ketone solvent, a nitrile solvent, an amide solvent, a sulfoxide solvent, a sulfone solvent, water, or a combination of these solvents. Non-limiting examples of the ketone solvent include acetone, methyl ethyl ketone, and methyl isobutyl ketone. Non-limiting example of the nitrile solvent include acetonitrile. Non-limiting examples of the amide solvent include N,N-dimethylformamide ("DMF"), N,N-dimethylacetamide ("DME"), N-methylformamide, N-methylpyrrolidone ("NMP"), and hexamethylphosphoric triamide ("HMPA"). Non-limiting example of the sulfoxide solvent include dimethyl sulfoxide ("DMSO"). Non-limiting example of the sulfone solvent include sulfolane.

The reaction of (Z)-2,3-benzofuran-dione $O^3$-methyl dioxime (11B) with 2-haloethanol to form (Z)-benzofuran-2,3-dione $O^2$-(2-hydroxyethyl) $O^3$-methyl dioxime (12B) may be carried out at a temperature of about 20° C. to about 100° C., and specifically about 70° C. to about 85° C.

In the above process, the (Z)-benzofuran-2,3-dione $O^2$-(2-hydroxyethyl) $O^3$-methyl dioxime (12B) may be treated with a base to form (Z)-(5,6-dihydro-1,4,2-dioxazin-3-yl)(2-hydroxyphenyl)methanone O-methyl oxime (15). The base may be a metal hydroxide, such as lithium hydroxide, sodium hydroxide, potassium hydroxide, or a combination thereof.

The reaction of the (Z)-benzofuran-2,3-dione $O^2$-(2-hydroxyethyl) $O^3$-methyl dioxime (12B) to form (Z)-(5,6-dihydro-1,4,2-dioxazin-3-yl)(2-hydroxyphenyl)methanone O-methyl oxime (13) may be carried out at a temperature of about 20° C. to about 100° C., and specifically from about 65° C. to about 75° C.

This invention is further illustrated by the following examples that should not be construed as limiting.

EXAMPLES

An exemplary approach to fluoxastrobin is illustrated in Scheme 1. According to Scheme 1, the synthesis begins with chlorination of diethyl malonate (1) with a suitable chlorinating agent, for example, sulfuryl chloride. The resulting diethyl 2-chloromalonate (2) is converted to diethyl 2-fluoromalonate (3) with a suitable fluorinating reagent, such as a hydrogen fluoride-triethylamine complex. The ensuing cyclization in formamide provides 5-fluoropyrimidine-4,6-diol (4), which is treated with a suitable chlorinating agent, for example phosphorus oxychloride to give 4,6-dichloro-5-fluoropyrimidine (5). As further indicated in Scheme 2, 4,6-dichloro-5-fluoropyrimidine (5) is reacted with (E)-(5,6-dihydro-1,4,2-dioxazin-3-yl)(2-hydroxyphenyl)methanone O-methyl oxime (13) in an appropriate solvent and in the presence of a base to yield (E)-(2-((6-halo-5-fluoropyrimidin-4-yl)oxy)phenyl)(5,6-dihydro-1,4,2-dioxazin-3-yl) methanone O-methyl oxime (14), which is further reacted with 2-chlorophenol to give fluoxastrobin. As described above, the last two steps of the synthesis may be carried out as a one-pot process, i.e. without isolation of the intermediate, (E)-(2-((6-halo-5-fluoropyrimidin-4-yl)oxy)phenyl)(5,6-dihydro-1,4,2-dioxazin-3-yl)methanone O-methyl oxime (14).

Scheme 1

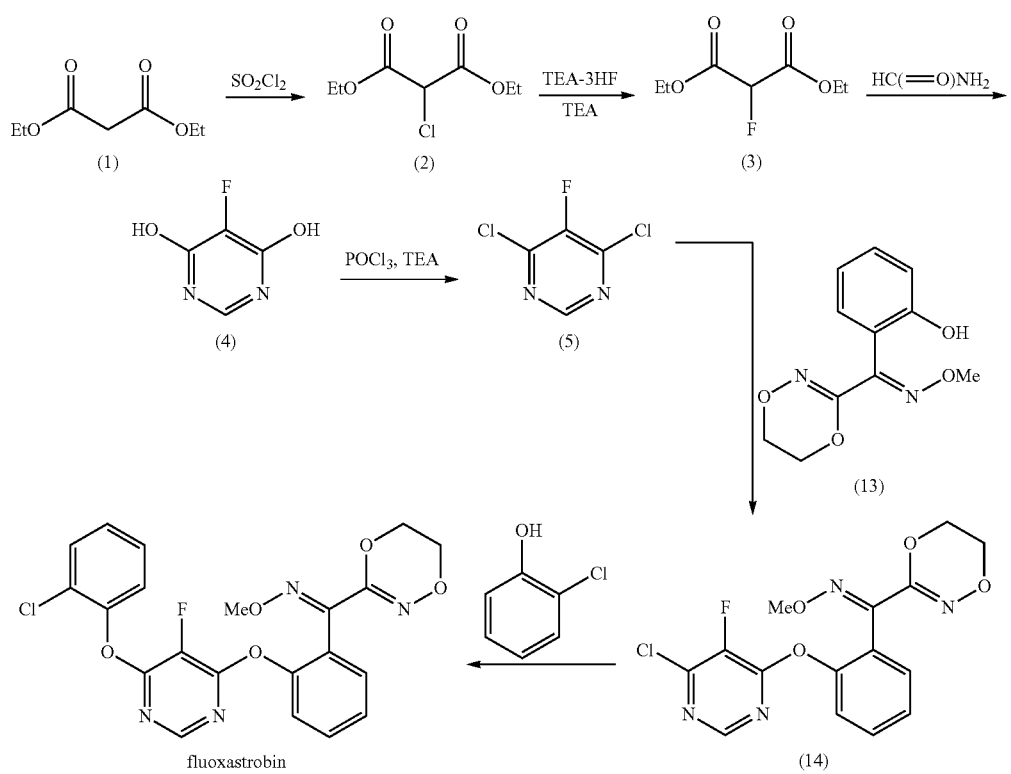

A synthesis of (E)-(5,6-dihydro-1,4,2-dioxazin-3-yl)(2-hydroxyphenyl)methanone O-methyl oxime (13) is illustrated in Scheme 2A. According to the synthesis, methyl salicylate reacts with ethyl chloro acetate in the presence of potassium carbonate to give methyl 2-(2-ethoxy-2-oxoethoxy)benzoate (6). Hydrolysis of methyl 2-(2-ethoxy-2-oxoethoxy)benzoate (6) followed by a consecutive cyclization of 2-(carboxymethoxy)benzoic acid (7) with acetic anhydride in the presence of sodium acetate gives benzofuran-3-yl acetate (8) which is converted to benzofuran-3(2H)-one (9) by methanolysis. Treatment of benzofuran-3(2H)-one (9) with O-methylhydroxylamine and sodium acetate affords benzofuran-3(2H)-one O-methyl oxime (10) which is oxidized with tert-butyl nitrate in hydrochloric acid to yield (3E)-benzofuran-2,3-dione O$^3$-methyl dioxime (11A). In the presence of potassium hydroxide, (3E)-benzofuran-2,3-dione O$^3$-methyl dioxime (11A) opens ethylene oxide resulting (3E)-benzofuran-2,3-dione O$^2$-(2-hydroxyethyl) O$^3$-methyl dioxime (12A) that undergoes potassium hydroxide-catalyzed cyclization to provide (E)-(5,6-dihydro-1,4,2-dioxazin-3-yl)(2-hydroxyphenyl)methanone O-methyl oxime (13).

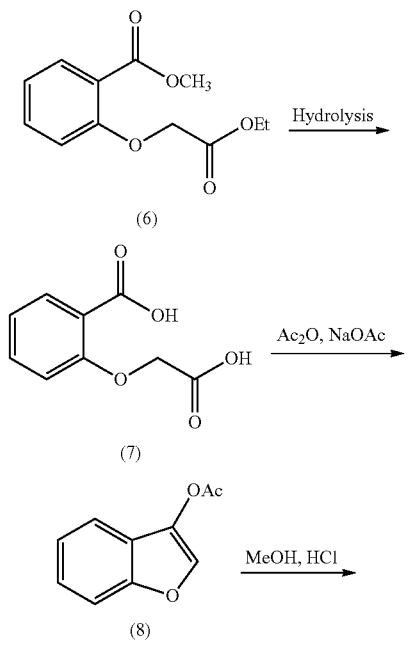

Scheme 2A

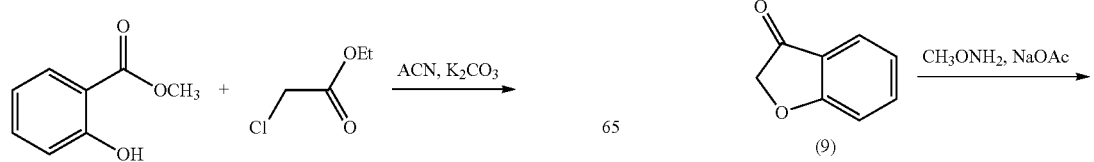

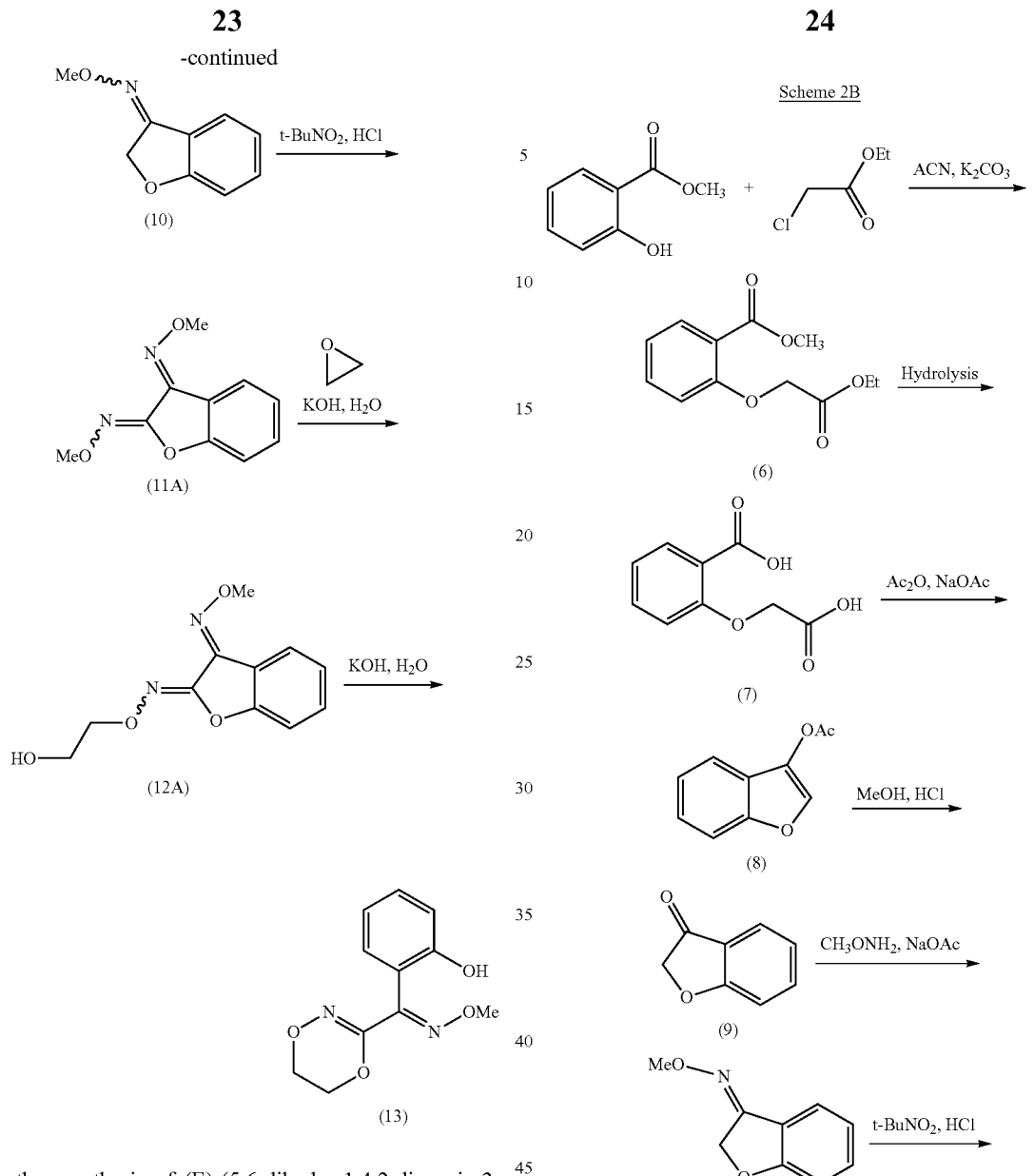

Another synthesis of (E)-(5,6-dihydro-1,4,2-dioxazin-3-yl)(2-hydroxyphenyl)methanone O-methyl oxime (13) is illustrated in Scheme 2B. According to the synthesis, methyl salicylate reacts with ethyl chloroacetate in the presence of potassium carbonate to give methyl 2-(2-ethoxy-2-oxoethoxy)benzoate (6). Hydrolysis of methyl 2-(2-ethoxy-2-oxoethoxy)benzoate (6) followed by a consecutive cyclization of 2-(carboxymethoxy)benzoic acid (7) with acetic anhydride in the presence of sodium acetate gives benzofuran-3-yl acetate (8) which is converted to benzofuran-3(2H)-one (9) by methanolysis. Treatment of benzofuran-3(2H)-one (9) with O-methylhydroxylamine and sodium acetate affords benzofuran-3(2H)-one O-methyl oxime (10) which is oxidized with tert-butyl nitrate in hydrochloric acid to yield exclusively or predominantly (3E)-benzofuran-2,3-dione O$^3$-methyl dioxime (11A). In the presence of potassium hydroxide and 2-haloethanol, the (3E)-benzofuran-2,3-dione O$^3$-methyl dioxime (11A) may form (3E)-benzofuran-2,3-dione O$^2$-(2-hydroxyethyl) O$^3$-methyl dioxime (12A), which may undergo potassium hydroxide-catalyzed cyclization to provide (E)-(5,6-dihydro-1,4,2-dioxazin-3-yl)(2-hydroxyphenyl)methanone O-methyl oxime (13).

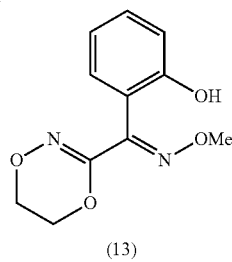 [SMILES: CO/N=C(/C1=NOCCO1)c1ccccc1O]

(13)

Fluoxastrobin may further be prepared as described in Scheme 3. Particularly, 4,6-dichloro-5-fluoropyrimidine (5) is reacted with 2-chlorophenol in an appropriate solvent and in the presence of a suitable base to give intermediate 4-chloro-6-(2-chlorophenoxy)-5-fluoropyrimidine (17) which is further reacted with (E)-(5,6-dihydro-1,4,2-dioxazin-3-yl)(2-hydroxyphenyl)methanone O-methyl oxime (13) to give fluoxastrobin.

Scheme 3

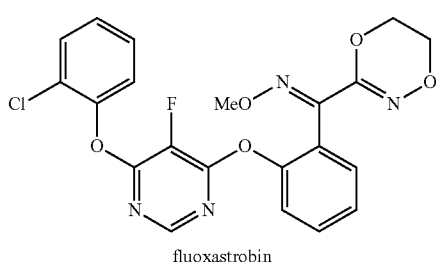

As shown in Scheme 4, fluoxastrobin may be prepared by sequentially reacting 4,6-dichloro-5-fluoropyrimidine (5) with (Z)-(5,6-dihydro-1,4,2-dioxazin-3-yl)(2-hydroxyphenyl)methanone O-methyl oxime (15) and thereafter with 2-chlorophenol to give (Z)-fluoxastrobin, which under appropriate conditions undergoes isomerization to fluoxastrobin.

Scheme 4

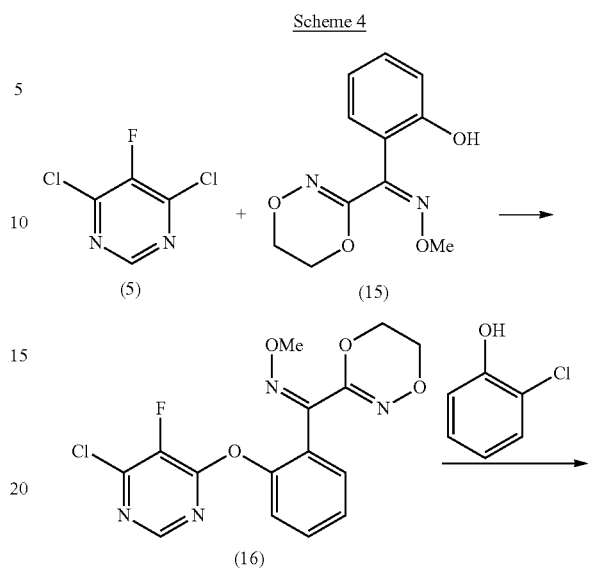

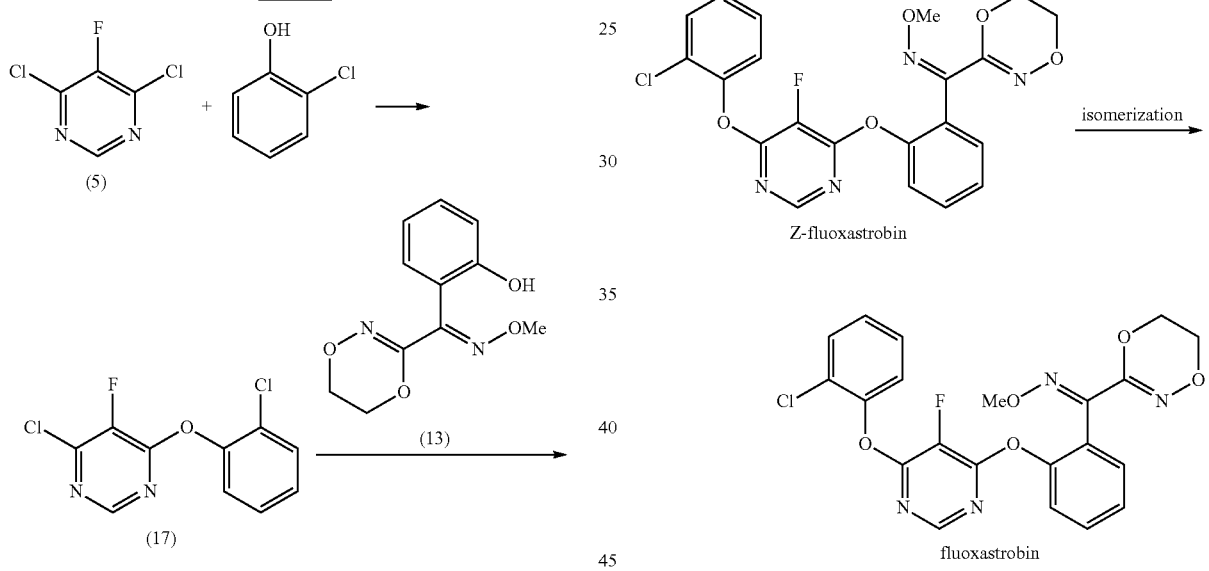

As further shown in Scheme 5, fluoxastrobin may be prepared by sequentially reacting 4,6-dichloro-5-fluoropyrimidine (5) with 2-chlorophenol that gives 4-chloro-6-(2-chlorophenoxy)-5-fluoropyrimidine (17) which on further reaction with (Z)-(5,6-dihydro-1,4,2-dioxazin-3-yl)(2-hydroxyphenyl)methanone O-methyl oxime (15) gives (Z)-fluoxastrobin, which under appropriate conditions may undergo isomerization to fluoxastrobin.

Scheme 5

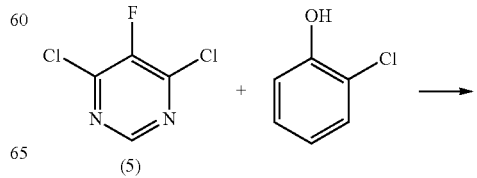

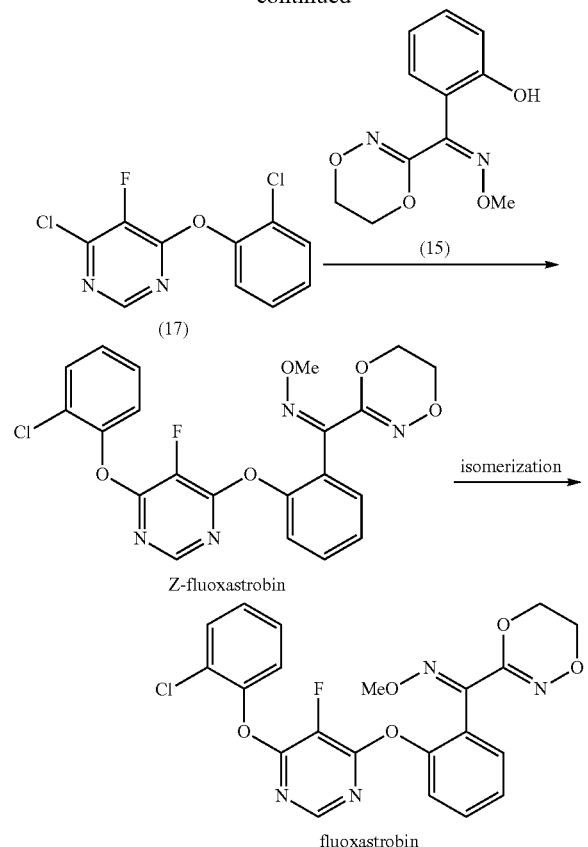

Z-fluoxastrobin fluoxastrobin

Synthesis of fluoxastrobin is further illustrated by the following experimental procedures:

Methyl 2-(2-ethoxy-2-oxoethoxy)benzoate (6)

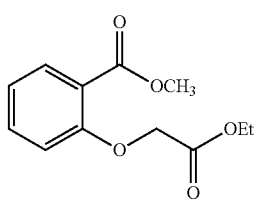

Chloroethyl acetate was slowly added to a mixture of methyl salicylate (100 g, 0.657 mol) and $K_2CO_3$ (100 g, 0.723 mol) in DMF (400 mL) at ambient temperature (20-30° C.). The reaction mixture was heated at 65-75° C. for 12-18 h. The progress of the reaction was monitored by HPLC analysis. Upon completion of reaction, the inorganics were filtered off and washed with DMF. DMF was recovered from the filtrate to obtain the product meeting the desired specifications. Yield—91-95%.

IR $(cm^{-1})$ 2985.71m, 1725.89s, 1598.81s, 1489.10s, 1448.49s, 1378.78m, 1300.25m, 1250.90m, 1193.64s, 1136.53w, 1088.35s, 959.50w, 834.93w, 756.49s, 706.30w, 658.81w. $^1$H NMR (400 MHz; $CDCl_3$) δ 1.306-1.271 (t, J=3.2 Hz, 3H), 3.906 (s, 3H), 4.292-4.238 (q, 2H), 4.713 (s, 2H), 6.897-6.877 (d, J=8 Hz, 1H), 7.068-7.028 (m, 1H,), 7.464-7.420 (m, 1H), 7.844-7.820 (dd, 1H, J=8 Hz). HPLC Purity: 98.63%.

2-(Carboxymethoxy)benzoic acid (7)

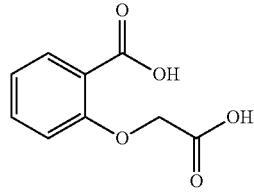

To a solution of aqueous NaOH (40 g, 0.838 mol) in water (300 mL) was slowly added methyl 2-(2-ethoxy-2-oxoethoxy)benzoate(6) (100 g, 0.419 mol) at 20-30° C. (exothermicity observed up to 50° C.), and thereafter the reaction mixture was stirred for 1-2 h. The progress of the reaction was monitored by the HPLC analysis. Upon completion of the reaction, the reaction mixture was acidified with diluted (1:1 by volume) $H_2SO_4$ (50 mL) to pH=2-3 at 20-35° C. The crude product was precipitated out, upon aging under stirring for 1 h at 20-30° C., the crude product was filtered and washed with water to obtain the product meeting the desired specifications. Yield—71-87%.

IR (KBr) $(cm^{-1})$ 3467.78w, 3178.72m, 2756.30w, 1743.43s, 1678.65s, 1367.36s, 1236.72s, 1056.69s. $^1$H NMR (400 MHz; DMSO-d6) δ 4.734 (s, 2H), 6.975-6.954 (d, J=8.4 Hz, 1H), 7.008-6.954 (m, 1H), 7.457-7.413 (m, 1H), 7.633-7.610 (m, J=1.6 Hz, 1H), 12.791 (bs, 2H). MS (EI) m/z: 195.2 (M−1); MS (EI) (m/z): 195.2 (M−1), 137.2, 117, 97. HPLC Purity: 99.605%.

Benzofuran-3-yl acetate (8)

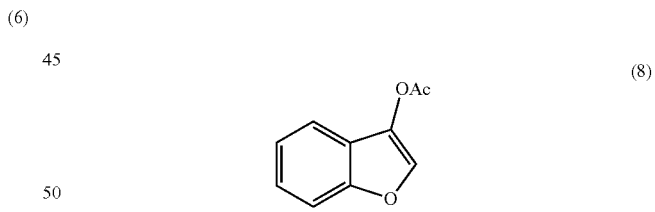

To acetic anhydride (300 mL) was added 2-(carboxymethoxy)benzoic acid (7) (100 g, 0.510 mol) at ambient temperature and heated to 130-140° C. The reaction temperature was maintained for 14-20 h under stirring. The progress of the reaction was monitored by the HPLC analysis. Upon completion of the reaction, the reaction mixture was cooled to 50-80° C., acetic anhydride was recovered at 50-80° C. at reduced pressure and the crude product was extracted with dichloromethane (500 mL). The dichloromethane layer was recovered completely to obtain the product meeting the desired specifications. Yield—76-85%.

IR $(cm^{-1})$ 3060.43w, 1759.45s, 1577.24s, 1449.18s, 1361.45s, 1179.20s, 1090.38s, 890.75, 742.41. $^1$H NMR (400 MHz; DMSO-d6) δ 2.384 (s, 3H), 7.332-7.292 (dd, 1H), 7.411-7.37 (dd, 1H), 7.62-7.576 (dd, J=9 Hz, 2H), 8.2 (s, 1H). GC-MS (EI) m/z: 176. HPLC Purity: 99.81%.

Benzofuran-3(2H)-one (9)

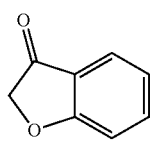

(9)

To a solution of benzofuran-3-yl acetate (8) (100 g, 1.42 mol) in methanol (350 mL) was added diluted (7.5%) $H_2SO_4$ (500 mL) at ambient temperature followed by heating to reflux for 1-3 h. The progress of the reaction was monitored by HPLC analysis. Upon completion of the reaction, the reaction mixture was cooled, filtered, and the slurry was washed with water, and vacuum dried to obtain the product meeting the desired specifications. Yield—83-100%.

IR (cm$^{-1}$) 2935.34, 1725.66, 1468.50, 1193.97. $^1$H NMR (400 MHz; DMSO) δ 4.807 (s, 2H), 7.176-7.138 (t, 1H), 7.303-7.283 (d, J=8 Hz, 1H), 7.657-7.635 (m, 1H), 7.748-7.705 (m, 1H). GC-MS (EI) m/z: 134.13. M.P.: 101-103° C. HPLC Purity: 99.51%.

Benzofuran-3(2H)-one O-methyl oxime (10)

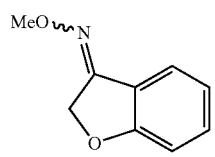

(10)

To a solution of benzofuran-3(2H)-one (9) (100 g, 0.745 mol) in methanol (700 mL) was added O-methyl hydroxylamine hydrochloride (68.5 g, 0.820 mol) and NaOAc (67.3 g, 0.820 mol) at ambient temperature followed by heating to reflux for 1-3 h. The progress of the reaction was monitored by the HPLC analysis. Upon completion of the reaction, the inorganics were filtered off, and methanol was recovered from the filtrate to provide residue. The residue was subjected to extractive work-up using dichloromethane (500 mL) and water (1 L) followed by recovery of the organic layer to obtain the product meeting the desired specifications. Yield—75-83%.

IR (cm$^{-1}$) 3070.02, 2898.40, 1604.89s, 1398.80s, 1537.36, 1465.17, 1041.49, 985.45s, 747.70s, 628.55s, 554.54s. $^1$H NMR (400 MHz; CDCl$_3$) δ 3.990 (s, 3H), 5.081 (s, 2H), 6.997-6.931 (m, 1H), 7.354-7.311 (m, 1H), 7.610-7.589 (m, J=7.8 Hz, 1H). MS (EI) m/z: 164 (M+1); MS (EI) (m/z): 164 (M+1), 132.9. M.P: 35-37° C. HPLC Purity: 98.92%.

(3E)-Benzofuran-2,3-dione O$^3$-methyl dioxime (11A)

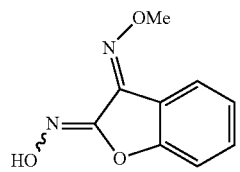

(11A)

To a ~13% solution of HCl in ethyl acetate (173 g, 0.613 mol) was added t-BuNO$_2$ (69.5 g, 0.675 mol) at 0-5° C. followed by the addition of benzofuran-3(2H)-one O-methyl oxime (10) (100 g, 0.613 mol) solution in ethyl acetate (400 mL) at 0-35° C. The progress of the reaction was monitored by the HPLC analysis. Upon completion of the reaction, the product was isolated by extractive work-up using ethyl acetate-water system that complies with the desired specifications. Yield—70-73%.

IR (cm$^{-1}$) 3243.39s, 3109.24m, 2935.39m, 2830.17m, 1599.15s. $^1$H NMR (400 MHz; CDCl$_3$) δ 4.112 (s, 3H), 7.259-7.221 (m, J=7.6 Hz, 1H), 7.347-7.327 (d, J=8 Hz, 1H), 7.605-7.563 (m, 1H), 8.043-8.022 (m, J=7.6 Hz, 1H), 11.351 (s, 1H). MS (EI) m/z: 193.1 (M+1); MS (EI) (m/z): 193.1 (M+1), 195.3, 175.9, 162.1, 149.2. M.P: 180-182° C. HPLC Purity: 99.84%.

(3Z)-Benzofuran-2,3-dione O$^3$-methyl dioxime (11B)

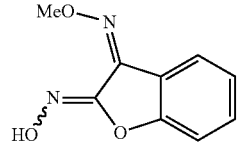

(11B)

To a stirred suspension of NaH (60% suspension; 8.1 g; 202.4 mmole) in DMF (300 ml) was slowly added n-butyl nitrite (20.87 g; 202.4 mmole) at 0 to 5° C. The resultant reaction mass was stirred for 10-15 min at the same temperature. Thereafter, benzofuran-mono-oxime solution (Compound 10, 30 g; 184 mmole) in DMF (30 ml) was slowly added maintaining the reaction temperature at 0 to 5° C. The reaction mass thereto was stirred for 30 min at 0 to 5° C. followed by stirring at 20-30° C. for additional 2-4 hr. The reaction was monitored by HPLC, and on completion of the reaction, the reaction mass was quenched with DM water (300 ml) at 0 to 10° C. The pH of reaction mass was adjusted to 1-2 using 50% aq. sulphuric acid solution at 0 to 5° C. The resulting suspension was stirred for 30 min at 5 to 10° C. Precipitation thus obtained was filtered and slurry washed with DM water (3×60 ml). The product was dried at 60-70° C. to afford 27.3 g (77.32% of theoretical yield) of (3Z)-Benzofuran-2,3-dione O$^3$-methyl dioxime (11B) in good to high chemical purity. Reaction monitoring by HPLC (% area): (3Z)-benzofuran dioxime (11B): 81.78% and (3E)-benzofuran dioxime (11A): 2.19%. Isolated product HPLC purity (% area): (3Z)-benzofuran dioxime (11B): 98.61% and (3E)-benzofuran dioxime (11A): 0.77%.

(3E)-Benzofuran-2,3-dione O²-(2-hydroxyethyl) O³-methyl dioxime (12A)

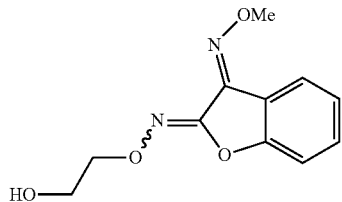

(12A)

To a solution of (3E)-benzofuran-2,3-dione O³-methyl dioxime (11A) (100 g, 0.520 mol) in DMSO (300 mL) was added 2-chloroethanol (50.31 g, 0.624 mol) followed by the addition of K₂CO₃ (100.6 g, 0.728 mol) at ambient temperature. The reaction mixture was stirred at 75-80° C. for 10-12 h. The progress of the reaction was monitored by the HPLC analysis. Upon completion of the reaction, the reaction mixture was quenched in water (2 L) and stirred at 20-30° C. for 1 h. The product was filtered, the slurry was washed with water, and suck dried to obtain the product meeting the desired specifications. Yield—83-87%.

IR (cm⁻¹, KBr) 3434.29s, 3078.21w, 2939.71s, 2819.94w, 1594.86s, 1456.72s, 1345.45m, 1301.57w, 1064.99s, 933.28w, 868.16w. ¹H NMR (CDCl₃, 400 MHz) δ 2.126-2.140 (t, J=5.6 Hz, 1H), 3.974-3.980 (m, 2H), 4.220 (s, 3H), 4.379-4.389 (m, 2H), 7.162-7.196 (m, 2H), 7.448-7.487 (t, J=8 Hz, 1H), 8.056-8.076 (d, J=8 Hz, 1H). ¹³NMR (CDCl₃, 400 MHz) δ 59.534 (—CH₂—), 64.342, 77.543 (—CH₂—), 111.742, 118.106, 124.788, 128.187, 134.436, 142.573, 147.753, 157.036. MS (EI) m/z 236.8 (M+1); MS2 (EI) m/z 237, 193.1, 162.0, 144.0 130.1, 119.1, 104.1, 90.0, 65.2. HPLC (Area %): 99.47%. M.P. 89-91° C.

(3Z)-Benzofuran-2,3-dione O²-(2-hydroxyethyl) O³-methyl dioxime (12B)

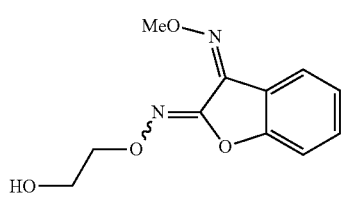

(12B)

To a solution of (3Z)-benzofuran-2,3-dione O³-methyl dioxime (11B) (100 g, 0.520 mol) in DMSO (300 mL) was added 2-chloroethanol (50.31 g, 0.624 mol) followed by the addition of K₂CO₃ (100.6 g, 0.728 mol) at ambient temperature. The reaction mixture was stirred at 75-80° C. for 10-12 h. The progress of the reaction was monitored by the HPLC analysis. Upon completion of the reaction, the reaction mixture was quenched in water (2 L) and stirred at 20-30° C. for 1 h. The crude product was filtered, the slurry was washed with water, and suck dried to obtain the product meeting the desired specifications. Yield—83-87%.

¹H NMR (CDCl₃, 400 MHz) δ 3.663-3.698 (m, 2H), 4.118 (s, 3H), 4.167-4.191 (t, J=4.8 Hz, 2H), 4.797-4.822 (t, J=4.8 Hz, 1H), 7.233-7.270 (t, J=7.6 Hz, 1H), 7.328-7.348 (d, J=8 Hz, 1H) 7.521-7.559 (t, J=8 Hz, 1H), 7.641-7.659 (d, J=7.2 Hz, 1H). ¹³NMR (CDCl₃, 400 MHz) δ 64.379, 69.349, 82.456, 116.550, 125.329, 126.351, 129.486, 137.692, 144.660, 150.969, 161.219. MS (EI) m/z 237.0 (M+1).

(E)-(5,6-Dihydro-1,4,2-dioxazin-3-yl)(2-hydroxyphenyl)methanone O-methyl oxime (13)

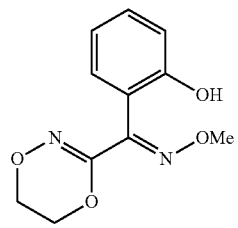

(13)

To the slurry of (3E)-benzofuran-2,3-dione O²-(2-hydroxyethyl) O³-methyl dioxime (12A)(100 g, 0.0423 mol) in water (400 mL) was added NaOH (25.3 g, 0.0635 mol) in water (200 mL) at 60-70° C. followed by stirring the reaction mixture at 80-85° C. for 1-2 h. The progress of the reaction was monitored by the HPLC analysis. Upon completion of the reaction, the reaction mixture was cooled to room temperature and acidified using 50% acetic acid (100 mL) to pH=5.0 to 5.5. The reaction mixture was stirred at room temperature for 1 h, the solid was filtered and washed with water followed by drying at 50-60° C. to obtain the product meeting the desired specifications. Yield—88-98%.

IR (cm⁻¹, KBr) 3449.71s, 2977.41w, 2939.54w, 1584.48s, 1453.48s, 1354.02m, 1186.98m, 1089.72m, 1111.90m, 1046.19s, 998.09m, 906.95m, 809.57w, 759.61w. ¹H NMR (CDCl₃, 400 MHz) δ 4.098 (s, 3H), 4.194-4.215 (t, J=4 Hz, 2H), 4.182-4.503 (t, J=5.2 Hz, 2H), 6.244 (s, 1H), 6.957-7.001 (m, 2H), 7.212-7.229 (d, J=7.8 Hz, 1H), 7.336-7.357 (m, 1H). ¹³NMR (CDCl₃, 400 MHz) δ 63.536, 64.100, 64.621, 117.718, 120.224, 130.352, 131.508, 148.369, 152.639, 153.733. MS (EI) m/z 237.0 (M+1); MS2 (EI) m/z 205.0, 178.1, 161.1, 145.1, 133.0, 119.0. HPLC (Area %): 99.29%. M.P. 159-161° C.

(Z)-(5,6-Dihydro-1,4,2-dioxazin-3-yl)(2-hydroxyphenyl)methanone O-methyl oxime (15)

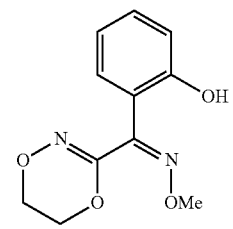

(15)

To the slurry of (3Z)-benzofuran-2,3-dione O²-(2-hydroxyethyl) O³-methyl dioxime (12B) (100 g, 0.0423 mol) in water (400 mL) was added NaOH (25.3 g, 0.0635 mol) in water (200 mL) at 60-70° C. followed by stirring the reaction mixture at 80-85° C. for 1-2 h. The progress of the reaction was monitored by the HPLC analysis. Upon completion of the reaction, the reaction mixture was cooled to room temperature and acidified using 50% acetic acid (100 mL) to pH=5.0 to 5.5. The reaction mixture was stirred at room temperature for 1 h, the solid was filtered and washed with water followed by drying at 50-60° C. to obtain the product meeting the desired specifications. Yield—88-98%.

$^1$H NMR (CDCl$_3$, 400 MHz) δ 3.960 (s, 3H), 4.149-4.169 (t, J=4 Hz, 2H), 4.411-4.431 (t, J=4 Hz, 2H), 6.844-6.907 (m, 4H), 7.270-7.313 (m, 1H), 7.367-7.390 (dd, J=1.2 Hz, J=1.6 Hz, 1H). HPLC (Area %): 98.93%. M.P. 110-114° C.

(E)-(2-((6-Chloro-5-fluoropyrimidin-4-yl)oxy)phenyl)(5,6-dihydro-1,4,2-dioxazin-3-yl)methanone O-methyl oxime (14)

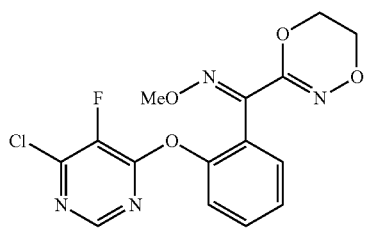

(14)

To a solution of 4,6-dichloro-5-fluoropyrimidine (DCFP) (100 g, 0.564 mol) in toluene (500 mL) was added (Z)-(5,6-dihydro-1,4,2-dioxazin-3-yl)(2-hydroxyphenyl)methanone O-methyl oxime (15) (77.8 g, 0.466 mol), K$_2$CO$_3$ (76 g, 0.55 mol), followed by the addition of DMF (50 mL) at ambient temperature. The reaction mixture was stirred at 80-85° C. for 1-2 h. The progress of the reaction was monitored by the HPLC analysis. Upon completion of the reaction, the reaction mixture was washed with water (500 mL) and 10% brine solution (250 mL) to obtain the product in toluene layer meeting the desired specifications. Yield—88-98%.

IR (cm$^{-1}$, KBr) 3075.01w, 2980.39w, 2940.78s, 2824.82w, 2410.77w, 1559.81s, 1445.46s, 1415.78m, 1304.99m, 1180.73s, 1110.89w, 1092.02w, 1053.57s, 1001.30m, 964.01m, 908.97m, 764.16m. $^1$H NMR (DMSO d$^6$, 400 MHz) δ 3.664 (s, 3H), 4.034-4.054 (t, J=4 Hz, 2H), 4.343-4.363 (t, J=4.4 Hz, 2H), 7.358-7.381 (m, 2H), 7.439-7.459 (d, J=8 Hz, 1H), 7.517-7.552 (m, 1H), 8.469 (s, 1H). $^{13}$C NMR (DMSO d$^6$, 400 MHz) δ 62.855, 64.411, 64.535, 123.116, 123.526, 126.182, 128.613, 129.31, 130.758, 131.083, 140.823, 143.494, 145.771, 146.173, 146.32, 148.682, 151.895, 152.429, 152.546, 157.671, 157.764. MS (EI) m/z 366.9 (M+1); MS2 (EI) m/z 334.9, 291.1, 275.3, 248.4, 223.0, 188.2. HPLC (Area %): 97.41%. M.P. 83-85° C.

(Z)-(2-((6-chloro-5-fluoropyrimidin-4-yl)oxy)phenyl)(5,6-dihydro-1,4,2-dioxazin-3-yl)methanone O-methyl oxime (16

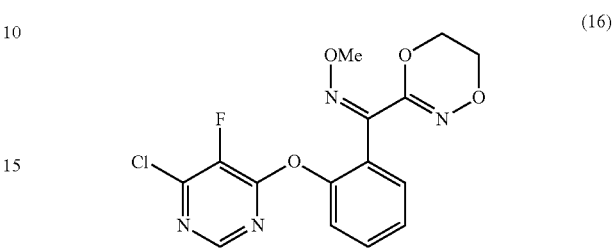

(16)

To a solution of 4,6-dichloro-5-fluoropyrimidine (DCFP) (100 g, 0.564 mol) in toluene (500 mL) was added (E)-(5,6-dihydro-1,4,2-dioxazin-3-yl)(2-hydroxyphenyl)methanone O-methyl oxime (13) (77.8 g, 0.466 mol), K$_2$CO$_3$ (76 g, 0.55 mol), followed by the addition of DMF (50 mL) at ambient temperature. The reaction mixture was stirred at 80-85° C. for 1-2 h. The progress of the reaction was monitored by the HPLC analysis. Upon completion of the reaction, the reaction mixture was washed with water (500 mL) and 10% brine solution (250 mL) to obtain the product in toluene layer meeting the desired specifications. Yield—88-98%.

(E)-(2-((6-(2-chlorophenoxy)-5-fluoropyrimidin-4-yl)oxy)phenyl)(5,6-dihydro-1,4,2-dioxazin-3-yl)methanone O-methyl oxime [Fluoxastrobin]

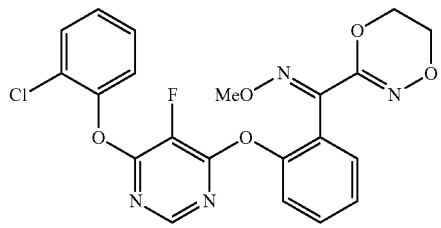

fluoxastrobin

To a solution of (E)-(2-((6-chloro-5-fluoropyrimidin-4-yl)oxy)phenyl)(5,6-dihydro-1,4,2-dioxazin-3-yl)methanone O-methyl oxime (14)(100 g, 0.564 mol) in toluene was added 2-chlorophenol (54 g, 0.846 mol), K$_2$CO$_3$ (50 g, 0.733 mol), and DMF (50 mL) at ambient temperature. The reaction mixture was stirred at 50-60° C. for 3-4 h. The progress of the reaction was monitored by the HPLC analysis. Upon completion of the reaction, aqueous NaOH (10%) (200 mL) was charged followed by water (300 mL). The mixture was stirred and the toluene layer was separated. The toluene layer was washed with a solution of brine (600 mL). The final toluene layer was recovered completely to get the crude product. To the above crude product, methanol was charged and heated to 60° C. until the clear solution is formed. The solution was stirred at room temperature to get the pure product precipitated. The pure fluoxastrobin product was filtered and washed with methanol. The product was further dried to obtain the pure fluoxastrobin product meeting the desired specifications. Yield—75-88%.

IR (cm$^{-1}$, KBr) 3072.99w, 2981.58w, 2936.76s, 2819.79w, 2502.01w, 1601.14s, 1572.37s, 1447.88s, 1305.43m, 1268.11m, 1217.15m, 1191.21m, 1092.60m, 1049.05m, 1001.26w, 910.25w, 762.81w. $^{1}$H NMR (CDCl$_3$, 400 MHz) δ 3.846 (s, 3H), 4.170-4.160 (t, J=4 Hz, 2H), 4.464-4.484 (t, J=4 Hz, 2H), 7.261-7.295 (m, 2H), 7.322-7.409 (2, 4H), 8.069 (s, 1H). $^{13}$C NMR (CDCl$_3$, 400 MHz) δ 63.103, 64.153, 64.550, 122.659, 123.259, 123.823, 125.712, 127.150, 127.397, 128.094, 130.511, 130.679, 130.776, 131.473, 134.138, 146.004, 148.166, 148.943, 150.354, 150.478, 151.819, 157.395, 157.466, 157.783, 157.854. MS (EI) m/z 459.1 (M+1); MS2 (EI) m/z 427.1, 383.0, 366.9, 342.1, 306.2, 246.0, 231.1, 188.0. HPLC (Area %): 99.40%. M.P. 108-112° C.

(Z)-(2-((6-(2-chlorophenoxy)-5-fluoropyrimidin-4-yl)oxy)phenyl)(5,6-dihydro-1,4,2-dioxazin-3-yl)methanone O-methyl oxime[(Z)-fluoxastrobin]

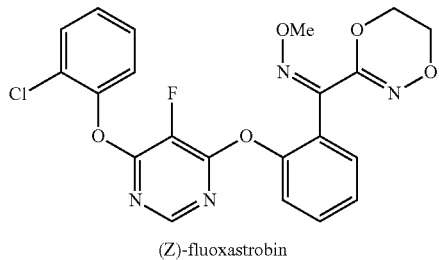 [SMILES: CO/N=C(\C1=NOCCO1)c1ccccc1Oc1ncnc(Oc2ccccc2Cl)c1F]

(Z)-fluoxastrobin

Isomerisation of (Z)-Fluoxastrobin to (E)-Fluoxastrobin using methane sulphonic acid. To a stirred solution of (Z)-Fluoxastrobin (0.3 g; 0.65 mmole) in acetonitrile (3 ml) was dropwise added methane sulphonic acid (0.04 ml, 0.65 mmole) at an ambient temperature. The reaction mixture was stirred for 2-3 hr at the same temperature. The progress of reaction was monitored by thin layer chromatography (TLC). Dichloromethane (5 ml) and DM water (5 ml) was added to reaction mass at an ambient temperature. After vigorous stirring, the layers were separated. The aqueous layer was back extracted with dichloromethane (5 ml) and the combined dichloromethane layer was washed with 10% aqueous sodium bicarbonate solution (20 ml) followed by washing with 10% brine solution (20 ml). Dichloromethane was distilled off at reduced pressure at 35-45° C. to obtain (E)-Fluoxastrobin as crude product (0.25 g, 83% of theoretical yield). Crude fluoxastrobin on purification in ethanol affords pure (E)-Fluoxastrobin. Isolated product HPLC purity (% area): (Z)-fluoxastrobin: 1.02% and (E)-fluoxastrobin: 95.92%.

Isomerisation of (Z)-Fluoxastrobin to (E)-Fluoxastrobin using phosphoric acid. To a stirred solution of (Z)-Fluoxastrobin (0.25 g; 0.54 mmole) in acetonitrile (4 ml) was dropwise added phosphoric acid (0.03 g, 0.54 mmole) at an ambient temperature. The reaction mixture was stirred for 2-3 hr at the same temperature. Progress of reaction was monitored by thin layer chromatography/HPLC. Dichloromethane (5 ml) and DM water (5 ml) was added to reaction mass at an ambient temperature. After vigorous stirring, layers were separated. The aqueous layer was back extracted with dichloromethane (5 ml). The combined dichloromethane layers were washed with 10% aq. Sodium bicarbonate solution (20 ml) followed by washing with 10% brine solution (20 ml). Dichloromethane was distilled off at reduced pressure at 40-45° C. to obtained (E)-Fluoxastrobin (0.22 g, 88% of Theoretical yield). Reaction monitoring by HPLC (% area): (Z)-Fluoxastrobin: 6.79% and (E)-Fluoxastrobin: 88.84%. Isolated product HPLC purity (% area): (Z)-Fluoxastrobin: 6.94% and (E)-Fluoxastrobin: 84.43%.

IR (cm$^{-1}$, KBr) 3066.28w, 2981.58w, 2939.36s, 2825.71w, 2500.61w, 1602.36s, 1572.76s, 1441.05s, 1297.05m, 1218.17m, 1116.52s, 1046.15m 1000.86w, 904.73s, 764.71w. $^{1}$H NMR (CDCl$_3$, 400 MHz) δ 3.983 (s, 3H), 4.163-4.218 (t, 2H), 4.432-4.440 (t, J=3.2 Hz, 2H), 7.217-7.352 (m, 4H), 7.371-7.390 (m, 2H), 7.483-7.516 (m, 2H), 7.702-7.722 (d, J=8 Hz, 1H), 8.016 (s, 1H). MS (EI) m/z 459.1 (M+1); MS2 (EI) m/z 427.0, 382.9, 366.7, 340.0, 305.8, 246.1, 188.0. HPLC (Area %): 99.11%. M.P. 150-152° C.

The present disclosure is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}$C, $^{13}$C, and $^{14}$C.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

The terms "a" and "an" do not denote a limitation of quantity, but rather denote the presence of at least one of the referenced item. The term "or" means "and/or." The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

As used herein, the term "halogen" refers to fluorine, chlorine, bromine, or iodine.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A process for preparing fluoxastrobin, comprising:
(i) reacting benzofuran-3(2H)-one O-methyl oxime (10) with an alkyl nitrite in the presence of an acid to form (3E)-2,3-benzofuran-dione O³-methyl dioxime (11A) as a predominant isomer;

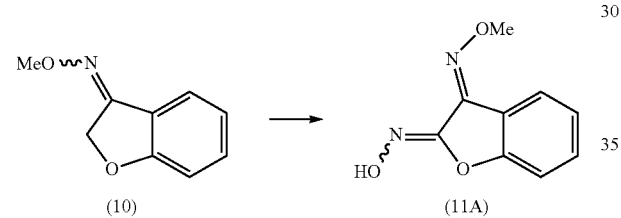

(ii) reacting the (3E)-2,3-benzofuran-dione O³-methyl dioxime (11A) with 2-haloethanol to form (3E)-benzofuran-2,3-dione O²-(2-hydroxyethyl) O³-methyl dioxime (12A); and

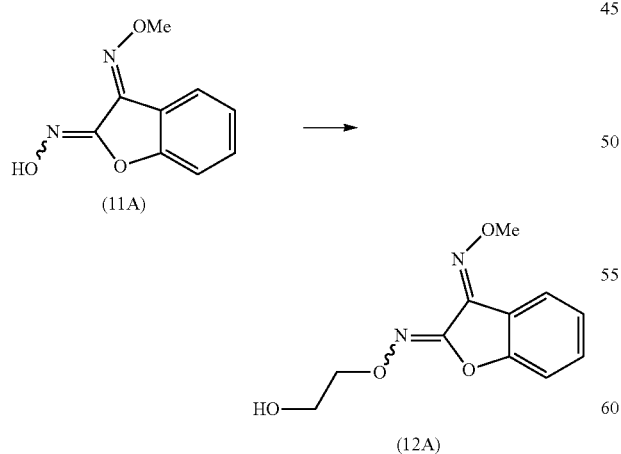

(iii) reacting the (3E)-benzofuran-2,3-dione O²-(2-hydroxyethyl) O³-methyl dioxime (12A) with a base to form (E)-(5,6-dihydro-1,4,2-dioxazin-3-yl)(2-hydroxyphenyl)methanone O-methyl oxime (13)

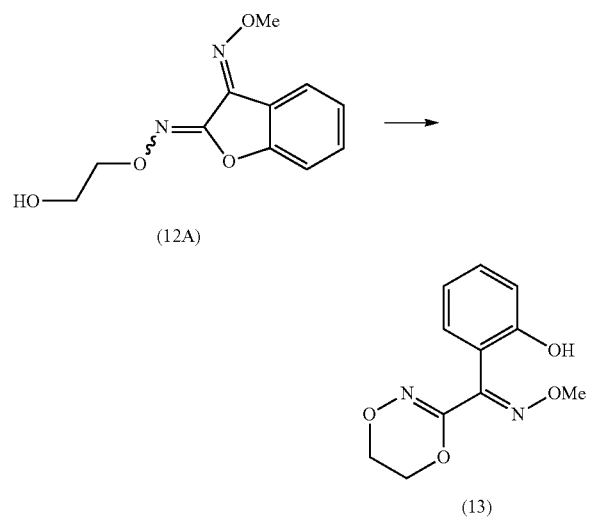

(iv) reacting a 4,6-di-halo-5-fluoro-pyrimidine (5), wherein X₁ is halogen, with (E)-(5,6-dihydro-1,4,2-dioxazin-3-yl)(2-hydroxyphenyl)methanone O-methyl oxime (13), in the presence of a solvent and optionally in the presence of a base, to form an (E)-(2-((6-halo-5-fluoropyrimidin-4-yl)oxy)phenyl)(5,6-dihydro-1,4,2-dioxazin-3-yl)methanone O-methyl oxime (14):

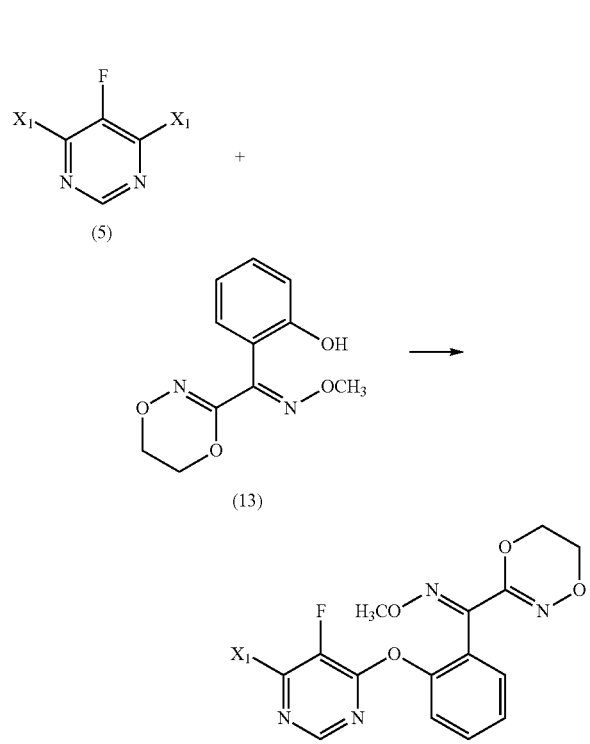

(v) reacting the (E)-(2-((6-halo-5-fluoropyrimidin-4-yl)oxy)phenyl)(5,6-dihydro-1,4,2-dioxazin-3-yl)methanone O-methyl oxime (14) with 2-chlorophenol, in the presence of a solvent and optionally in the presence of a base, to form fluoxastrobin:

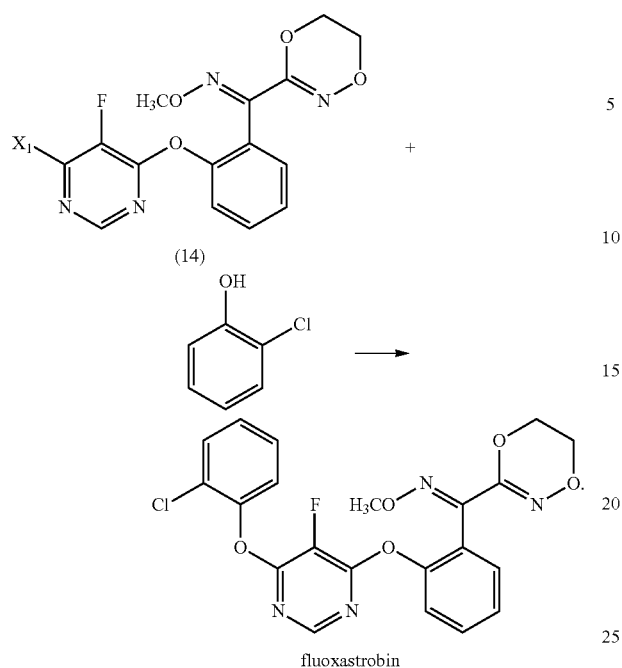

fluoxastrobin

2. The process of claim 1, wherein X$_1$ is chlorine.

3. The process of claim 1, wherein the reacting the (E)-(2-((6-halo-5-fluoropyrimidin-4-yl)oxy)phenyl)(5,6-dihydro-1,4,2-dioxazin-3-yl)methanone O-methyl oxime (14) with 2-chlorophenol is carried out in the presence of a tertiary amine.

4. The process of claim 3, wherein the tertiary amine is 1,4-diazabicyclo[2.2.2]octane.

5. The process of claim 1, wherein steps (ii) to (v) are carried out as a one-pot process.

6. The process of claim 1, wherein the alkyl nitrite is n-butyl nitrite or t-butyl nitrite.

7. The process of claim 1, wherein the acid comprises hydrochloric acid, sulfuric acid, methanesulfonic acid, or phosphoric acid.

8. The process of claim 1, wherein a content of the (3E)-2,3-benzofuran-dione O$^3$-methyl dioxime (11A) in a mixture of (3E)- and (3Z)-isomers is from 90% to 94%.

9. A process for preparing fluoxastrobin, comprising:

(i) reacting a 4,6-di-halo-5-fluoro-pyrimidine (5), wherein X$_1$ is halogen, with (Z)-(5,6-dihydro-1,4,2-dioxazin-3-yl)(2-hydroxyphenyl)methanone O-methyl oxime (15), optionally in the presence of a solvent and optionally in the presence of a base, to form a (Z)-(2-((6-halo-5-fluoropyrimidin-4-yl)oxy)phenyl)(5,6-dihydro-1,4,2-dioxazin-3-yl)methanone O-methyl oxime (16):

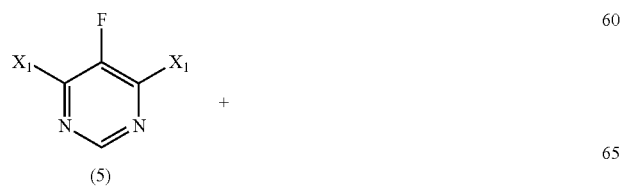

(5)

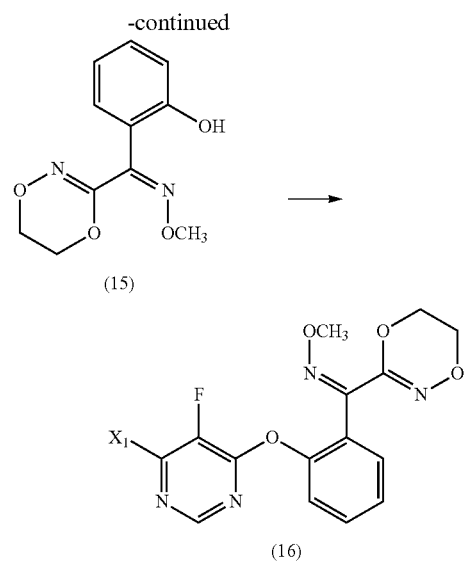

(ii) reacting the (Z)-(2-((6-halo-5-fluoropyrimidin-4-yl)oxy)phenyl)(5,6-dihydro-1,4,2-dioxazin-3-yl)methanone O-methyl oxime (16) with 2-chlorophenol, optionally in the presence of a solvent and optionally in the presence of a base, to form (Z)-fluoxastrobin:

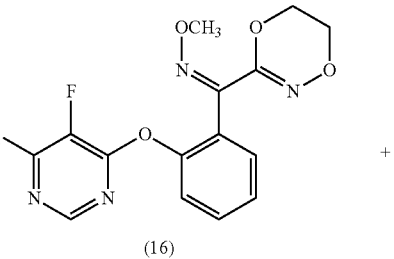

(16)

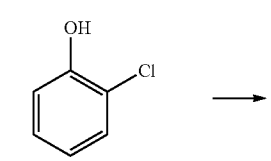

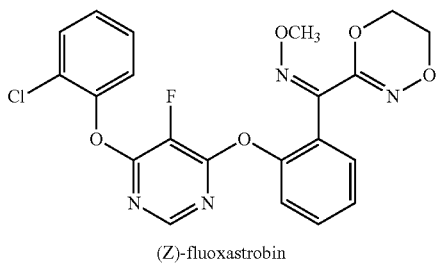

(Z)-fluoxastrobin (iii) isomerizing the (Z)-fluoxastrobin to form fluoxastrobin:

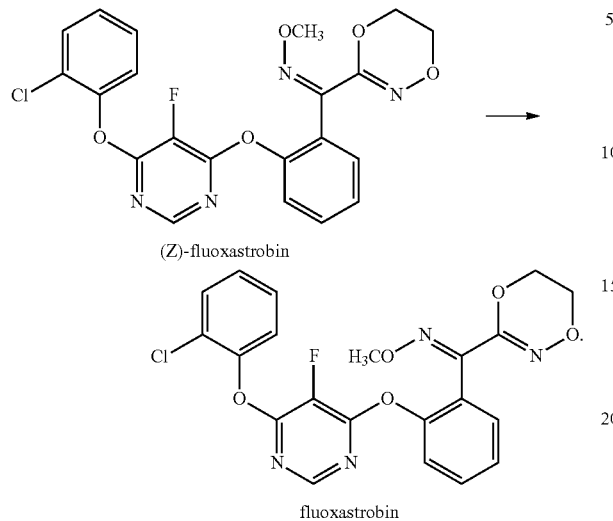

10. A process for preparing fluoxastrobin, comprising:

(i) reacting a 4,6-di-halo-5-fluoro-pyrimidine (5), wherein $X_1$ is halogen, with 2-chlorophenol, optionally in the presence of a solvent and optionally in the presence of a base, to form a 4-halo-6-(2-chlorophenoxy)-5-fluoropyrimidine (17):

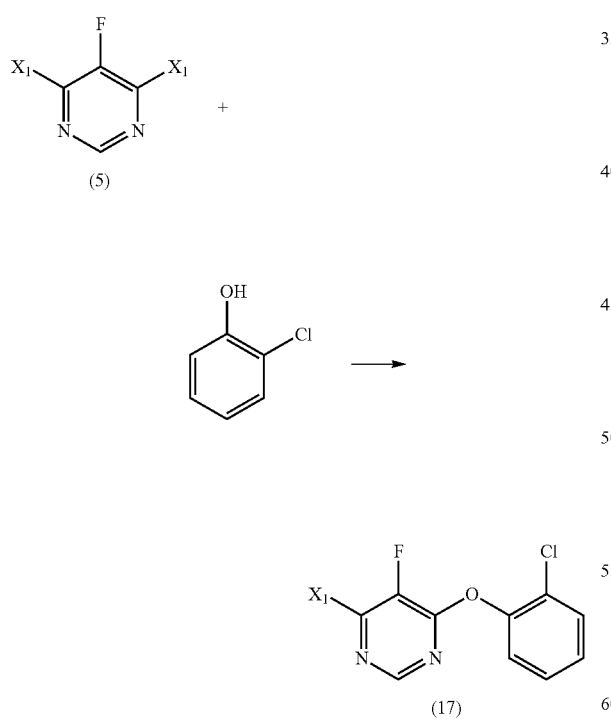

(ii) reacting the 4-halo-6-(2-chlorophenoxy)-5-fluoropyrimidine (17) with (Z)-(5,6-dihydro-1,4,2-dioxazin-3-yl)(2-hydroxyphenyl)methanone O-methyl oxime (15), optionally in the presence of a solvent and optionally in the presence of a base, to form (Z)-fluoxastrobin:

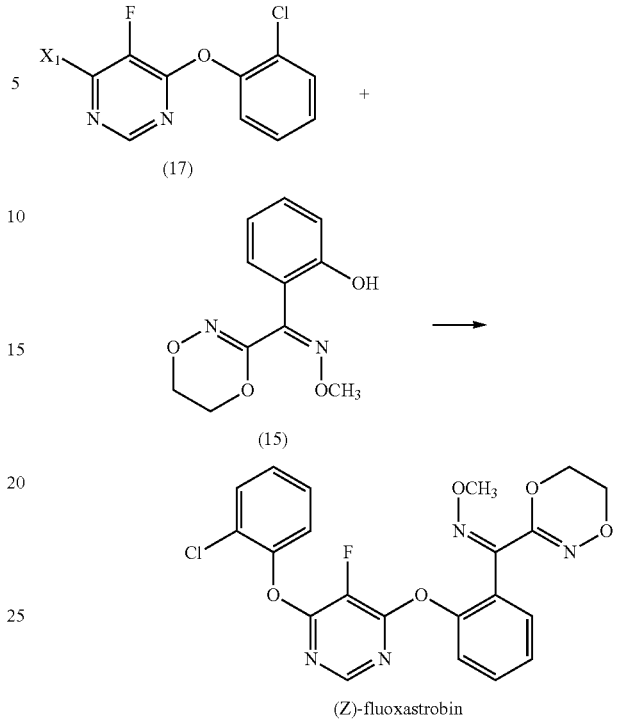

(iii) isomerizing the (Z)-fluoxastrobin to form fluoxastrobin:

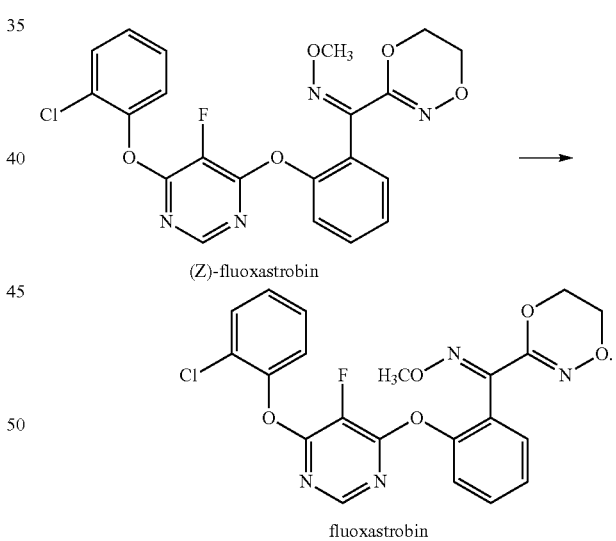

11. The process of claim 9 or 10, wherein the isomerizing (Z)-fluoxastrobin to form fluoxastrobin is carried out in the presence of a solvent, and optionally an acid catalyst.

12. The process of claim 9 or 10, wherein the (Z)-(5,6-dihydro-1,4,2-dioxazin-3-yl)(2-hydroxyphenyl)methanone O-methyl oxime (15) is prepared by:

(iv) reacting benzofuran-3(2H)-one O-methyl oxime (10) with an alkyl nitrite in the presence of a base to form (3Z)-2,3-benzofuran-dione $O^3$-methyl dioxime (11B) as a predominant isomer;

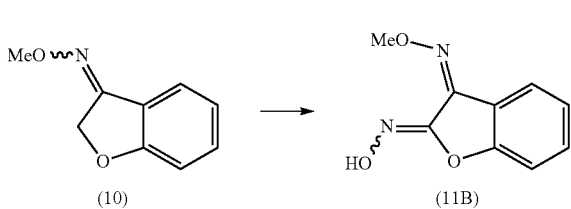 [SMILES: CON=C1COc2ccccc21 ; CO/N=C1\C(=NO)Oc2ccccc21]

(v) reacting the (3Z)-2,3-benzofuran-dione O³-methyl dioxime (11B) with 2-haloethanol to form (3Z)-benzofuran-2,3-dione O²-(2-hydroxyethyl) O³-methyl dioxime (12B); and

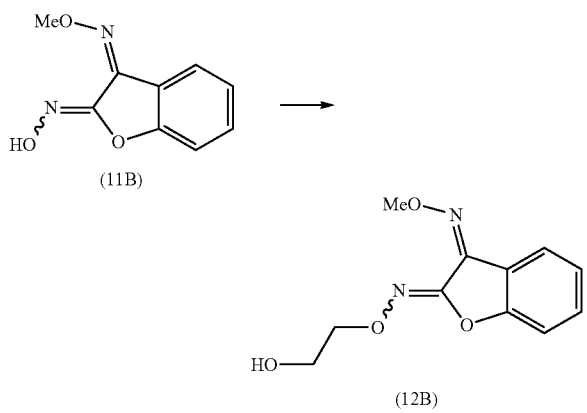

(vi) reacting the (3Z)-benzofuran-2,3-dione O²-(2-hydroxyethyl) O³-methyl dioxime (12B) with a base to form (Z)-(5,6-dihydro-1,4,2-dioxazin-3-yl)(2-hydroxyphenyl)methanone O-methyl oxime (15)

13. The process of claim 12, wherein the alkyl nitrite is n-butyl nitrite or t-butyl nitrite.

14. The process of claim 12, wherein the base in the reacting benzofuran-3(2H)-one O-methyl oxime (10) with an alkyl nitrite comprises a metal hydroxide, a metal hydride, and a metal alkoxide.

15. The process of any of claim 12, wherein a content of the (3Z)-2,3-benzofuran-dione O³-methyl dioxime (11B) in a mixture of (3E)- and (3Z)-isomers is 94% to 98%.

* * * * *